US011492622B2

(12) United States Patent
Weiss et al.

(10) Patent No.: US 11,492,622 B2
(45) Date of Patent: Nov. 8, 2022

(54) MICRORNA-BASED LOGIC GATES AND USES THEREOF

(71) Applicant: Massachusetts Institute of Technology, Cambridge, MA (US)

(72) Inventors: Ron Weiss, Newton, MA (US); Giulio Alighieri, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/032,259

(22) Filed: Sep. 25, 2020

(65) Prior Publication Data

US 2021/0095287 A1    Apr. 1, 2021

Related U.S. Application Data

(60) Provisional application No. 62/906,246, filed on Sep. 26, 2019.

(51) Int. Cl.
    *C12N 15/113*    (2010.01)
(52) U.S. Cl.
    CPC ...... *C12N 15/113* (2013.01); *C12N 2310/141* (2013.01); *C12N 2320/53* (2013.01)
(58) Field of Classification Search
    None
    See application file for complete search history.

(56) References Cited

U.S. PATENT DOCUMENTS

| 2009/0234109 | A1  | 9/2009 | Han et al. |       |
|--------------|-----|--------|------------|-------|
| 2013/0202532 | A1* | 8/2013 | Benenson   | G16B 25/10 |
|              |     |        |            | 424/9.1 |

FOREIGN PATENT DOCUMENTS

| WO | WO 2015/185691 A1 | 12/2015 | |
| WO | WO-2015183667 A1 * | 12/2015 | ............ C12N 15/11 |
| WO | WO 2018/165536 A1 | 9/2018 | |
| WO | WO 2019/027414 A1 | 2/2019 | |

OTHER PUBLICATIONS

Mohammadi Cell Systems 4, 207-218, pp. 1-27 (Year: 2017).*
Seelig et al. Science vol. 314, pp. 1585-1588 (Year: 2006).*
Lapique et al., Digital switching in a biosensor circuit via programmable timing of gene availability. Nat Chem Biol. Dec. 2014;10(12):1020-7. doi: 10.1038/nchembio.1680. Epub Oct. 14, 2014. PMID: 25306443; PMCID: PMC4232471.
Matsuura et al., Synthetic RNA-based logic computation in mammalian cells. Nat Commun. Nov. 19, 2018;9(1):4847. doi: 10.1038/s41467-018-07181-2. Erratum in: Nat Commun. Apr. 26, 2019;10(1):1950. PMID: 30451868; PMCID: PMC6242901.
Bartel, MicroRNAs: target recognition and regulatory functions. Cell. Jan. 23, 2009;136(2):215-33. doi: 10.1016/j.cell.2009.01.002. PMID: 19167326; PMCID: PMC3794896.
Miki et al., Efficient Detection and Purification of Cell Populations Using Synthetic MicroRNA Switches. Cell Stem Cell. Jun. 4, 2015;16(6):699-711. doi: 10.1016/j.stem.2015.04.005. Epub May 21, 2015. PMID: 26004781.

* cited by examiner

*Primary Examiner* — Brian Whiteman

(74) *Attorney, Agent, or Firm* — Wolf, Greenfield & Sacks, P.C.

(57) ABSTRACT

The present disclosure, at least in part, relates to a miRNA based logic gate that comprises an engineered RNA carrier that comprises an nuclear export signal, a target site for a first miRNA and a pre-miRNA sequence for a second miRNA. Also provided by the disclosure are recombinant viruses (e.g., recombinant adeno-associated viruses (rAAV)) for delivery of the miRNA based logic gates.

20 Claims, 15 Drawing Sheets

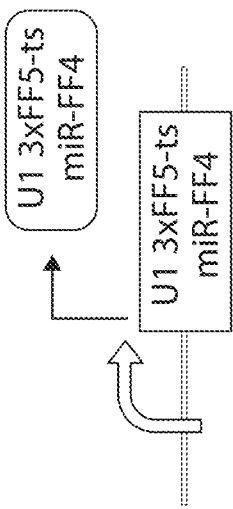
FIG. 4A
FIG. 4B
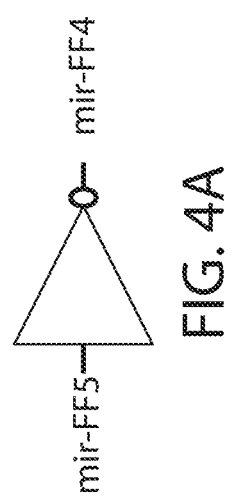
FIG. 4C

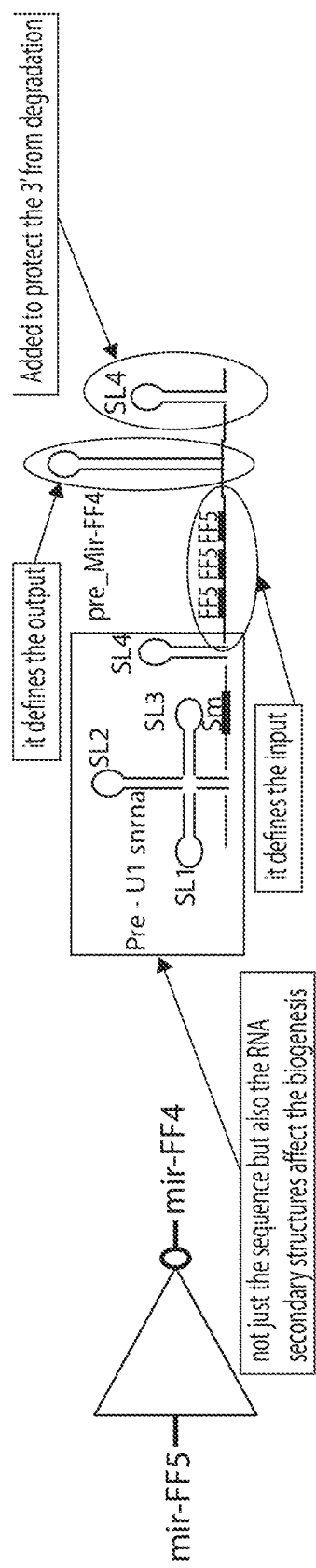
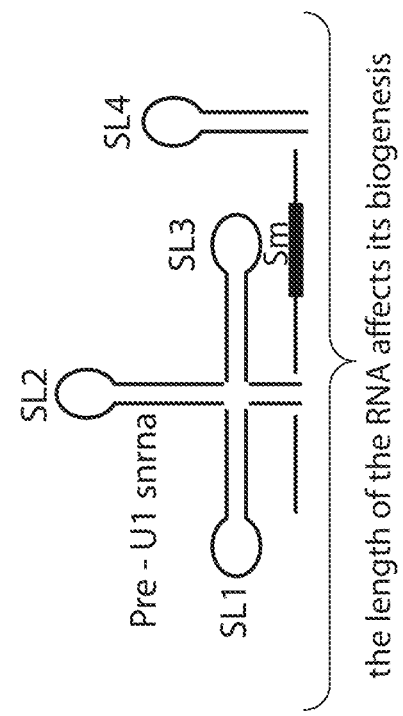
FIG. 5A
FIG. 5B

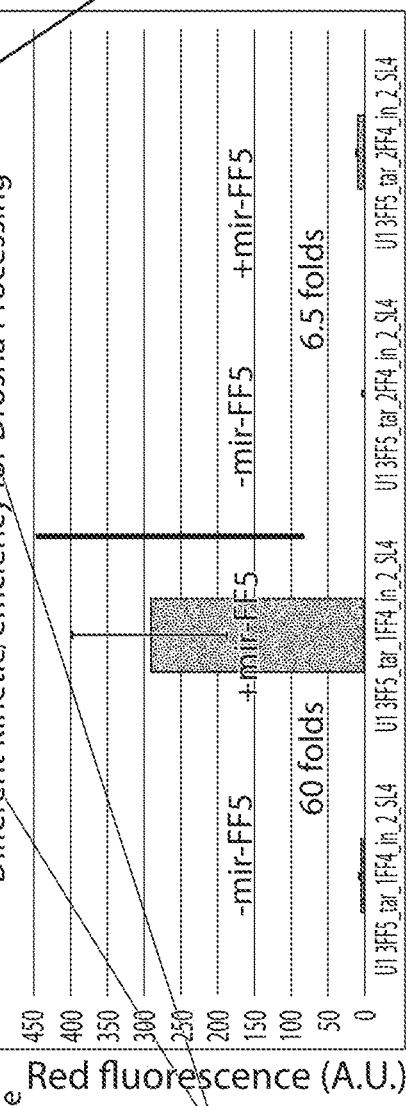

MICRORNA-BASED LOGIC GATES AND USES THEREOF

RELATED APPLICATION

This application claims the benefit under 35 U.S.C. § 119(e) of U.S. provisional application No. 62/906,246 filed Sep. 26, 2019, which is incorporated by reference herein in its entirety.

FEDERALLY SPONSORED RESEARCH

This invention was made with government support under CA207029 awarded by the National Institutes of Health. The government has certain rights in the invention.

BACKGROUND

Micro-RNA (miRNA) is a powerful tool widely used in biotechnologies and gene therapies for both therapeutic and diagnostic purposes. There is currently a growing and pressing need to engineer genetic circuits that allow a therapeutic miRNA agent to be expressed according to a certain miRNAs signature without the use of exogenous proteins, which may trigger unwanted and extremely dangerous immune responses in mammalian cells. Currently, there are no other technologies that allow mammalian cells to express a therapeutic miRNA according to a miRNAs biomarker signature without using exogenous proteins.

SUMMARY

The present disclosure, at least in part, relates to a miRNA based logic gates that allow a therapeutic miRNA agent to be expressed according to a certain miRNA signature without the use of exogenous proteins, which may trigger unwanted and extremely dangerous immune responses. These miRNA based logic gates are designed to sense the presence or absence of certain miRNAs in a cell and respond accordingly, exerting their activity only under desired conditions characterized by the presence or absence of certain cellular miRNAs. Conditional expression of therapeutic miRNAs allows the miRNA based logic gates described herein to be delivered systemically but activated only in target cells, reducing the chance of off-target effects that could compromise their safety as a gene therapy. Also with the disclosure are recombinant viruses (e.g., recombinant adeno-associated viruses (rAAV)) for delivery of the miRNA based logic gates.

In some aspects, the present disclosure provides an miRNA based logic gate comprising an engineered RNA carrier that comprises: (i) a nuclear export sequence or a nuclear import signal; (ii) a target site for a first microRNA (miRNA); and (iii) a pre-miRNA sequence of a second microRNA (miRNA). In some embodiments, the miRNA based logic gate is a NOT gate. In some embodiments, the miRNA based logic gate is a NOR gate. In some embodiments, the engineered RNA carrier further comprises a target site for a third miRNA. In some aspects, the present disclosure provides an miRNA based logic gate, wherein the miRNA logic gate is a miRNA-based NAND gate, which comprises two miRNA based NOT gate described herein.

In some aspects, the present disclosure provides an miRNA based logic gate, wherein the miRNA logic gate is a miRNA-based flip flop, which comprises two miRNA based NOR gates of claims or two miRNA based NAND gates described herein.

In some embodiments, the engineered RNA carrier is an mRNA or a non-coding RNA. In some embodiments, the non-coding RNA is selected from a group consisting of small nuclear RNA (snRNA), small non-coding RNA, viral cytosolic RNAs, viral nuclear RNAs, and RNAs capable of being shuttled back and forth from the cytosol and the nucleus of the cell. In some embodiments, the small nuclear RNA is pre-U1 snRNA, pre-U2 snRNA, pre-U3 snRNA, pre-U4 snRNA, pre-U5 snRNA, pre-U6 snRNA, pre-U7 snRNA, pre-U4atac snRNA, pre-U11 snRNA, or pre-U12 snRNA. In some embodiments, the small nuclear RNA is pre-U1 snRNA. In some embodiments, the mRNA is a viral nuclear RNA or a viral cytosolic RNA.

In some embodiments, the engineered RNA carrier further comprises a sequence that binds to the survival of motor neuron complex (SMN complex).

In some embodiments, the miRNA based logic gate further comprises a 3' cap.

In some aspects, the present disclosure also provides an engineered nuclei acid comprising a promoter operably linked to a nucleotide sequence encoding the miRNA based logic gate described herein.

In some aspects, the present disclosure also provides a recombinant virus comprising: a viral capsid containing a promoter operably linked to a nucleotide sequence encoding the miRNA based logic gate described herein. In some embodiments, the recombinant virus is a recombinant AAV (rAAV).

In some aspects, the present disclosure also provides a cell comprising the miRNA based NOT gate, the engineered nucleic acid, or the recombinant virus as described herein. In some embodiments, the cell is a prokaryotic cell. In some embodiments, the prokaryotic cell is a bacterial cell. In some embodiments, the cell is a eukaryotic cell. In some embodiments, the eukaryotic cell is a plant cell, an insect cell, or a mammalian cell. In some embodiments, the mammalian cell is a human cell. In some embodiments, the cell is a diseased cell. In some embodiments, the cell is from a specific tissue. In some embodiments, the cell expresses the first miRNA, and does not express the second miRNA. In some embodiments, the cell does not expresses the first microRNA, and expresses the second miRNA. In some embodiments, the cell expresses both the first and the second miRNA, and the downregulation of the first miRNA leads to the upregulation of the second miRNA. In some embodiments, the cell expresses both the first and the second miRNA, and the upregulation of the first miRNA leads to the downregulation of the second miRNA.

In some aspects, the present disclosure also provides a pharmaceutical composition, comprising the miRNA based logic gate, the engineered nucleic acid, the recombinant virus, or the cell, as described herein. In some embodiments, the pharmaceutical composition further comprises a pharmaceutically acceptable carrier.

In some aspects, the present disclosure also provides a method comprising delivering a miRNA based logic gate, the engineered nucleic acid, the recombinant virus, the cell, or the pharmaceutical composition, as described herein, to a subject in need thereof.

In some aspects, the present disclosure also provides a method for delivering a miRNA to a specific cell type in a subject in need thereof, comprising administering to the subject an effective amount of a miRNA based logic gate, the engineered nucleic acid, the recombinant virus, the cell, or the pharmaceutical composition, as described herein, to a subject in need thereof.

In some aspects, the present disclosure also provides a method for treating a disease in a subject in need thereof, comprising administering to the subject an effective amount of a miRNA based logic gate, the engineered nucleic acid, the recombinant virus, the cell, or the pharmaceutical composition, as described herein, to a subject in need thereof.

In some embodiments, the subject is a human or a non-human mammal. In some embodiments, the subject has or is at risk of having Alpha-1 antitrypsin deficiency, Hypercholesterolemia, Hepatitis B infection, Liver adenoma due to HIV infection, Hepatitis C virus infection, Ornithine transcarbamylase deficiency, Hepatocellular carcinoma, Amyotrophic lateral sclerosis, Spinocerebellar ataxia type 1, Huntington's disease, Parkinson disease, Spinal and Bulbar muscular atrophy, Pyruvate dehydrogenase deficiency, Hyperplasia, obesity, FSHD, Nerve Injury-induced Neuropathic Pain, Age-related macular degeneration, Retinitis pigmentosa, heart failure, cardiomyopathy, cold-induced cardiovascular dysfunction, Asthma, Duchenne muscular dystrophy, or prostate cancer.

BRIEF DESCRIPTION OF THE DRAWINGS

FIGS. 4A-4D shows the biogenesis of U1-based NOT-gate. FIG. 4A shows a NOT-gate where the input is mirFF5 and the output is mirFF4. FIG. 4B shows a truth-table of the NOT-gate in FIG. 4A. FIG. 4C shows the design of the U-1 based NOT-gate. FIG. 4D is a diagram showing how U1-based NOT-gate can be engineered including the analysis of its behavior at a biomolecular level. Drosha can process the pre-miRNA FF4, so the miRNA FF4 is expressed if and only if the miRNA FF5 is NOT expressed. In case the miRNA FF5 is expressed, the pre-miRNA FF4 is NOT shuttled back to the nucleus from the cytosol. Drosha is in the nucleus, so it canNOT process the pre-miRNA FF4 in the cytosol. However, the RISC is in the cytosol but is unable to process pre-miRNA directly. This results in miRNA FF4 NOT being expressed.

FIGS. 5A-5F show the RNA sequence and requirements for NOT-gate behavior. FIG. 5A shows U1 snRNA NOT-gate. FIG. 5B shows endogenous U1 snRNA. FIG. 5C shows the U1 snRNA NOT-gate RNA sequence. The following are requirements for NOT-gate behavior that are currently NOT predictable: total RNA length short enough to avoid the mRNA transport to the cytosol, Drosha NOT able to process pre-miRNA before the export to the cytosol, RISC able to target the RNA-carrier in the cytosol, Drosha able to process the pre-miRNA once back in the nucleus, biogenesis of the RNA-carrier NOT disrupted by the insertion of the RNA exogenous sequences, and pre-miRNA NOT degraded in the cytosol. The following are requirements for NOT-gate behavior that are currently predictable: RNA-carrier shuttled between the nucleus and cytosol without the use of exogenous proteins, RISC NOT able to load the pre-miRNA in the cytosol, and Drosha NOT able to process the pre-miRNA in the cytosol. FIGS. 5D-5F show experimental results of U1-based NOT-gate and its behavior.

FIG. 6A shows a single module miR-based NOT gate. FIG. 6B-6C describes one example that two miR-based NOT gates can be layered to produce an miRNA based NOR gate that can sense two individual input miRNAs and produce results accordingly. Further, FIG. 6D-6E shows other miR-based logic gate such as latch flip flop NAND gates, basic flip flop circuit NAND gates and oscillators using the miR-based NOT gate.

FIG. 7A shows the constructs that were transfected into cells, which encode 1) U6 Mir-FF5, 2) either U1 mir-FF4/3xFF5-ts or U1 mir-FF4/3xFF3-ts, 3) hEF1a Blue as transfection marker, and 4) hEF1a Red/3xFF4-ts as a reporter that can be downregulated in the presence of mir-FF4. FIG. 7B shows the structure of the two NOT gates, which can sense the presence of either mir-FF5 (left) or mir-FF3 (right), and the amount of Red fluorescent protein detected 4 days after transfection as measured by flow cytometry.

FIGS. 8A-8B show experimental results describing the behavior of two different NOT gates in cells. FIG. 8A shows the constructs that were transfected into cells, which encode 1) either U6 Mir-FF5 or negative control, 2) either U1 mir-FF4/3xFF5 or U1 2x mir-FF4/3xFF5, 3) hEF1a Blue as transfection marker, and 4) hEF1a Red/3xFF4-ts. FIG. 8B shows the structure of the two NOT gates that sense the presence of mir-FF5 and contain one copy of pre-mir-FF4 (left; Design A) or two copies of pre-mir-FF4 that each have a different design (right; Design A and Design B), and the amount of Red fluorescent protein detected 3 days after transfection with each set of constructs as measured by flow cytometry.

DETAILED DESCRIPTION

Figure 1C:
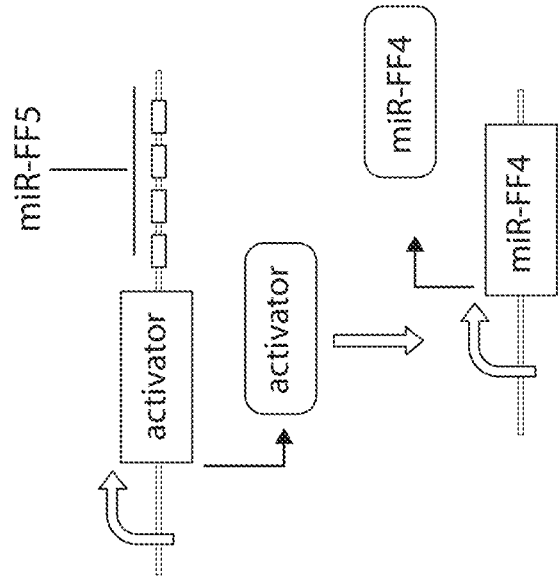
FIG. 1C shows how the NOT-gate that requires exogenous proteins.

The present disclosure, at least in part, relates to a miRNA based logic gates that allow a therapeutic miRNA agent to be expressed according to a certain miRNA signature without the use of exogenous proteins, which may trigger unwanted and extremely dangerous immune responses. Also provided by the present disclosure are recombinant viruses (e.g., recombinant adeno-associated viruses (rAAV)) for delivery of the miRNA based NOT gates.

I. Engineered miRNA Based NOT Logic Gates and Engineered Nucleic Acids Encoding the Same At least in part, the present disclosure relates to the microRNA (miRNA) based logic gates such as as NOT gates, NOR gates, NAND gates and oscillators. A NOT gate, as used herein, refers to the logic gates that take one input and produces as output its opposite. In some embodiments, the NOT gate described herein is an miRNA based NOT logic gate. As used herein, "a NOT gate" or "a NOT logic gate" is used interchangeably. An miRNA based NOT logic gate, refers to a NOT gate designed for expressing an output molecule (e.g., a second miRNA) in response to an input molecule (e.g., an first miRNA). A NOR gate, as used herein, refers to a logic gate that takes two or more inputs and produces as output only when all the input signals are not present. An miRNA based NOR logic gate, refers to a NOR gate designed for expressing an output molecule (e.g., a second miRNA) in response to two or more different input molecules (e.g., an first miRNA, a third miRNA, or more.). In some embodiments, the miRNA logic gates do not require an exogenous protein to facilitate its function. In some embodiments, the miRNA based NOT gate or the NOR gate can be layered to produce more sophisticated miRNA based logic gates capable of responding to various different input signals (e.g., several miRNA biomarker signatures). In some embodiments, two or more miRNA based NOT gates can be layered to produce a miRNA based NAND switch. For example, the two miRNA based NOT gates that composes of the miRNA based NAND switch may share the same output, but different input signals. In some embodiments, two miRNA based NAND gates can further form a "latch flip flop NAND gate," where the output of each NAND gate is one of the input of the other NAND gate. In some embodiments, multiple NOT gate can be connected to form an oscillator, where the output of the previous NOT gate is the input of the following NOT gate, and where the output of the last NOT gate is the input of the first NOT gate.

It can be appreciated any other designs of an miRNA based logic gate are within the scope of the present disclosure. In some embodiments, the miRNA based logic gate has 1, 2, 3, 4, 5, 6, 7, 8, 9, 10, 15, 20 or more basic miRNA based NOT gates and/or NOR gates.

In some embodiments, the miRNA based logic gates comprises a basic module. In some embodiments, the basic module is a miRNA based NOT gate. In some embodiments, the miRNA based NOT gate described herein, comprises an engineered RNA carrier. An engineered RNA carrier, as used herein, refers to an RNA molecule that is engineered to comprise the necessary elements for the RNA NOT gate to express an miRNA in response to an input. In some embodiments, the engineered RNA carrier can be shuttled back and forth to different regions of the cell. In some embodiments, once the engineered RNA carrier is transcribed, it can be shuttled from the nucleus of the cell to the cytosol. In some embodiments, the RNA carrier comprises: (i) a nuclear export sequence or a nuclear import signal; (ii) a target site for a first miRNA; and (iii) a pre-miRNA sequence of a second miRNA. In some embodiments, once the engineered RNA carrier is shuttled from the nucleus to the cytosol, the engineered RNA carrier is capable of sensing the presence or absence of the input signal (e.g., the first miRNA). In some embodiments, the presence of the input signal (e.g., the first miRNA) can lead to the engineered RNA carrier being targeted by the first miRNA, such that the biogenesis of the second miRNA is inhibited. In some embodiments, in the absence of the input signal (e.g., the first miRNA), the engineered RNA can be shuttled from the cytosol to another region of the cell (e.g., back to the nucleus or to another area of the cytosol) such that the biogenesis of the second miRNA can be initiated. In this process, no exogenous protein is required for the transportation of the engineered RNA carrier or the initiation of the miRNA biogenesis of the second miRNA. In some embodiments, the engineered RNA carrier further comprises a sequence that binds to the survival of motor neuron complex (SMN complex), such that the engineered RNA carrier can associate with the spliceosome complex and be shuttled back to the nucleus if the input signal (e.g., first miRNA) is absent in the cytosol. Once the engineered RNA carrier is shuttled back to the nucleus, the pre-miRNA sequence of the second miRNA can be cleaved by drosha, thus initiating downstream miRNA biogenesis for the second miRNA. In some embodiments, the basic module is a miRNA based NOR gate. In some embodiments, the engineered nucleic acid further comprises a target for a third miRNA to form a miRNA based NOR gate. A similar process would take place depends on the presence or absence of the first and the third miRNA in the cell. In some embodiments, the biogenesis of the second miRNA can only take place when neither the first nor the third miRNA are present in the cell.

Suitable RNAs that can be engineered into an miRNA based logic gate that comprises the engineered RNA carrier are those RNAs that can naturally be shuttled from one region of the cell to another region of the cell (e.g., from nucleus to cytosol, and back to nucleus). Non-limiting examples of RNAs that can be engineered as the miRNA based logic gate that comprises the engineered RNA carriers are protein coding mRNA or a non-coding RNA.

In some embodiments, the RNAs that can be engineered as the miRNA based logic gate that comprises the engineered RNA carriers is a protein coding mRNA. In some embodiments, the protein coding mRNA has or is engineered to have a target site for the first miRNA, and the protein coding mRNA is engineered to comprise a pre-miRNA sequence of a second miRNAIn some embodiments, the protein coding mRNA is a viral cytosolic RNAs from a DNA virus or a RNA virus. In some embodiments, the protein coding mRNA is viral nuclear RNAs from a DNA virus or a RNA virus. In some embodiments, such viral cytosolic RNAs comprises a nuclear import sequence. Non-limiting examples of DNA viruses are Baculoviridae, Papovaviridae, Polydnaviridae, Adenoviridae, Herpesviridae, phage, Ascoviridae, Ampullaviridae, Asfarviridae, Baculoviridae, Fuselloviridae, Globuloviridae, Guttaviridae, Hytrosaviridae, Iridoviridae, Lipothrixviridae, Nimaviridae, Poxviridae, Ampullaviridae, Bicaudaviridae, Clavaviridae, Fuselloviridae, Globuloviridae, Guttaviridae, Tristromaviridae, Anelloviridae, Circoviridae, Geminiviridae, Nanoviridae, Gemycircularvirus, Gemyduguivirus, Gemygorvirus, Gemykibivirus, Gemykolovirus, Gemykrogvirus, Gemykroznavirus, Gemytondvirus, Gemyvongvirus, or Turriviridae. Non-limiting examples of RNA viruses are HIV, ribovirus, Ebola virus disease, SARS, rabies, common cold, influenza, hepatitis C, hepatitis E, West Nile fever, polio or measles.

In other embodiments, the RNAs that can be engineered as the miRNA based logic gate that comprises the engineered RNA carrier is a non-coding RNA. A non-coding RNA (ncRNA) refers to a functional RNA molecule that is transcribed from DNA but logic translated into protein(s). Non-limiting ncRNAs include miRNA, siRNA, shRNA, small nuclear RNA (snRNA), piRNA, and lncRNA. In general, ncRNAs function to regulate gene expression at the transcriptional and post-transcriptional level. Examples of the non-coding RNA suitable to be engineered to the RNA carriers are, but not limited to, small nuclear RNA (snRNA), small non-coding RNA, and RNAs capable of being shuttled back and forth from the cytosol and the nucleus of the cell. In some embodiments, the non-coding RNA engineered as the miRNA based logic gate that comprises the engineered RNA carriers is small nuclear RNA (snRNA). In some embodiments, the small nuclear RNA that can be engineered to RNA carriers are pre-U1 snRNA, pre-U2 snRNA, pre-U3 snRNA, pre-U4 snRNA, pre-U5 snRNA, pre-U6 snRNA, pre-U7 snRNA, pre-U4atac snRNA, pre-U11 snRNA, or pre-U12 snRNA. In some embodiments, the snRNA engineered to RNA carrier is pre-U1 snRNA.

In part, the RNAs that can be engineered as the miRNA based logic gate that comprises the engineered RNA carriers of the present disclosure is designed to detect miRNA by incorporating target sites of the miRNA to be detected into different RNA carries. Expression of the microRNA leads to the degradation of RNA carrier encoding the second miRNA. In some embodiments, the miRNA based logic gate that comprises the engineered RNA carrier comprises a target site for the input signal (e.g., the first miRNA). A "microRNA target site" is a nucleotide sequence that is complementary to the nucleotide sequence of the microRNA. In some embodiments, microRNA targeting sites exist in messenger RNAs (mRNA), typically in the 3' untranslated regions of mRNAs. In some embodiments, miRNA target site can be engineered to a RNA molecule (e.g., the engineered RNA carrier herein). Binding of the microRNA to its target site in via sequence complementarity leads to silencing of an output molecule (e.g., the second miRNA) either via degrading the mRNA or suppressing translation of the mRNA (e.g., as described in Bartel et al., Cell 136 (2): 215-33 (2009), incorporated herein by reference) containing the microRNA binding sites. Herein, when microRNA target sites are referred in the context of the genetic circuits (i.e., in a context of DNA), it intends to mean the nucleotide sequence that encodes the microRNA target sites in the mRNA that is produced from the genetic circuit.

In some embodiments, the miRNA based logic gate that comprises the engineered RNA carrier comprises at least 1, at least 2, at least 3, at least 4, at least 5, at least 6, at least 7, at least 8, at least 9, or at least 10 target sites for the first miRNA. In some embodiments, the presence or absence, or levels of the first miRNA is miRNA biomarker signature for a specific tissue. In some embodiments, the presence or absence, or levels of the first miRNA is miRNA biomarker signature for a specific cell type in a tissue. In some embodiments, the presence or absence, or levels of the first miRNA is miRNA biomarker signature for a specific disease. In some embodiments, the microRNA biomarker signature may be expression levels of microRNAs that have no expression, or lower expression (e.g., at least 30% lower), and/or expression levels of microRNAs that express or have higher expression (e.g., at least 30% higher) in a cell or a cell type, compared to another cell or a different cell type, respectively. In some embodiments, the presence or absence of the first miRNA is miRNA biomarker signature for a specific cell type in a diseased tissue. Non-limiting examples of the tissues are lung tissue, skin tissue, breast tissue, connective tissue, brain tissue, gastrointestinal tissue, heart tissue, kidney tissue, etc. Non-limiting examples for specific cell types are epithelial cells, endothelial cells, fibroblasts, immune cells, etc. Non-limiting examples of a diseased cells are neo-plastic cells, infected cells, cells harboring genetic mutations, fibro genetic cells, etc. Methods of identifying a miRNA biomarker signature in a specific tissue, cell or disease are known in the art. Information about the sequences, origins, and functions of known microRNAs maybe found in publically available databases (e.g., mirbase.org/, all versions, as described in Kozomara et al., Nucleic Acids Res 2014 42:D68-D73; Kozomara et al., Nucleic Acids Res 2011 39:D152-D157; Griffiths-Jones et al., Nucleic Acids Res 2008 36:D154-D158; Griffiths-Jones et al., Nucleic Acids Res 2006 34:D140-D144; and Griffiths-Jones et al., Nucleic Acids Res 2004 32:D109-D111, including the most recently released version miRBase 21, which contains "high confidence" microRNAs). Non-limiting examples of microRNAs that are expressed in cells and are able to be detected by the engineered RNA carrier are: FF4, FF5, hsa-let-7a-2-3p, hsa-let-7a-3p, hsa-let-7a-5p, hsa-let-7b-3p, hsa-let-7b-5p, hsa-let-7c-5p, hsa-let-7d-3p, hsa-let-7d-5p, hsa-let-7e-3p, hsa-let-7e-5p, hsa-let-7f-1-3p, hsa-let-7f-2-3p, hsa-let-7f-5p, hsa-let-7g-3p, hsa-let-7g-5p, hsa-let-7i-5p, hsa-miR-1, hsa-miR-1-3p, hsa-miR-1-5p, hsa-miR-100-3p, hsa-miR-100-5p, hsa-miR-101-3p, hsa-miR-101-5p, hsa-miR-103a-2-5p, hsa-miR-103a-3p, hsa-miR-105-3p, hsa-miR-105-5p, hsa-miR-106a-3p, hsa-miR-106a-5p, hsa-miR-106b-3p, hsa-miR-106b-5p, hsa-miR-107, hsa-miR-10a-3p, hsa-miR-10a-5p, hsa-miR-10b-3p, hsa-miR-10b-5p, hsa-miR-1185-1-3p, hsa-miR-1185-2-3p, hsa-miR-1185-5p, hsa-miR-122a-5p, hsa-miR-1249-3p, hsa-miR-1249-5p, hsa-miR-124a-3p, hsa-miR-125a-3p, hsa-miR-125a-5p, hsa-miR-125b-1-3p, hsa-miR-125b-2-3p, hsa-miR-125b-5p, hsa-miR-126-3p, hsa-miR-126-5p, hsa-miR-12'7-3p, hsa-miR-12'71-3p, hsa-miR-12'71-5p, hsa-miR-1278, hsa-miR-128-1-5p, hsa-miR-128-2-5p, hsa-miR-128-3p, hsa-miR-1285-3p, hsa-miR-1285-5p, hsa-miR-1287-3p, hsa-miR-128'7-5p, hsa-miR-129-1-3p, hsa-miR-129-2-3p, hsa-miR-129-5p, hsa-miR-1296-3p, hsa-miR-1296-5p, hsa-miR-1304-3p, hsa-miR-1304-5p, hsa-miR-1306-3p, hsa-miR-1306-5p, hsa-miR-1307-3p, hsa-miR-1307-5p, hsa-miR-130a-3p, hsa-miR-130b-3p, hsa-miR-130b-5p, hsa-miR-132-3p, hsa-miR-132-5p, hsa-miR-133a-3p, hsa-miR-133a-5p, hsa-miR-133b, hsa-miR-134-3p, hsa-miR-134-5p, hsa-miR-135a-3p, hsa-miR-135a-5p, hsa-miR-135b-3p, hsa-miR-135b-5p, hsa-miR-136-3p, hsa-miR-136-5p, hsa-miR-138-1-3p, hsa-miR-138-5p, hsa-miR-139-3p, hsa-miR-139-5p, hsa-miR-140-3p, hsa-miR-140-5p, hsa-miR-141-3p, hsa-miR-141-5p, hsa-miR-142-3p, hsa-miR-142-5p, hsa-miR-143-3p, hsa-miR-143-5p, hsa-miR-144-3p, hsa-miR-144-5p, hsa-miR-145-5p, hsa-miR-146a-3p, hsa-miR-146a-5p, hsa-miR-147a, hsa-miR-148a-3p, hsa-miR-148a-5p, hsa-miR-148b-3p, hsa-miR-148b-5p, hsa-miR-149-3p, hsa-miR-144-3p, hsa-miR-150-3p, hsa-miR-150-5p, hsa-miR-151a-3p, hsa-miR-151a-5p, hsa-miR-152-3p, hsa-miR-152-5p, hsa-miR-154-3p, hsa-miR-154-5p, hsa-miR-155-3p, hsa-miR-155-5p, hsa-miR-15a-3p, hsa-miR-15a-5p, hsa-miR-15b-3p, hsa-miR-15b-5p, hsa-miR-16-1-3p, hsa-miR-16-2-3p, hsa-miR-16-5p, hsa-miR-17-3p, hsa-miR-17-5p, hsa-miR-181a-3p, hsa-miR-181a-5p, hsa-miR-181b-2-3p, hsa-miR-181b-5p, hsa-miR-181c-5p, hsa-miR-181d-3p, hsa-miR-181d-5p, hsa-miR-182-3p, hsa-miR-182-5p, hsa-miR-183-3p, hsa-miR-183-5p, hsa-miR-185-3p, hsa-miR-185-5p, hsa-miR-186-3p, hsa-miR-186-5p, hsa-miR-188-3p, hsa-miR-188-5p, hsa-miR-18a-3p, hsa-miR-18a-5p, hsa-miR-18b-5p, hsa-miR-1908-3p, hsa-miR-1908-5p, hsa-miR-190a-3p, hsa-miR-190a-5p, hsa-miR-191-3p, hsa-miR-191-5p, hsa-miR-1910-3p, hsa-miR-1910-5p, hsa-miR-192-

3p, hsa-miR-192-5p, hsa-miR-193a-3p, hsa-miR-193a-5p, hsa-miR-193b-3p, hsa-miR-193b-5p, hsa-miR-194-3p, hsa-miR-194-5p, hsa-miR-195-3p, hsa-miR-195-5p, hsa-miR-196a-3p, hsa-miR-196a-5p, hsa-miR-196b-3p, hsa-miR-196b-5p, hsa-miR-197-3p, hsa-miR-197-5p, hsa-miR-199a-3p, hsa-miR-199a-5p, hsa-miR-199b-3p, hsa-miR-199b-5p, hsa-miR-19a-3p, hsa-miR-19a-5p, hsa-miR-19b-1-5p, hsa-miR-19b-2-5p, hsa-miR-19b-3p, hsa-miR-200a-3p, hsa-miR-200a-5p, hsa-miR-200b-3p, hsa-miR-200b-5p, hsa-miR-200c-3p, hsa-miR-200c-5p, hsa-miR-202-3p, hsa-miR-202-5p, hsa-miR-203a-3p, hsa-miR-203a-5p, hsa-miR-204-5p, hsa-miR-208b-3p, hsa-miR-208b-5p, hsa-miR-20a-3p, hsa-miR-20a-5p, hsa-miR-20b-3p, hsa-miR-20b-5p, hsa-miR-21-5p, hsa-miR-210-3p, hsa-miR-210-5p, hsa-miR-211-3p, hsa-miR-211-5p, hsa-miR-2116-3p, hsa-miR-2116-5p, hsa-miR-212-3p, hsa-miR-214-3p, hsa-miR-215-5p, hsa-miR-217, JG_miR-218-1-3p, hsa-miR-218-5p, hsa-miR-219a-1-3p, hsa-miR-219a-2-3p, hsa-miR-219a-5p, hsa-miR-219b-3p, hsa-miR-219b-5p, hsa-miR-22-3p, hsa-miR-22-5p, hsa-miR-221-3p, hsa-miR-221-5p, hsa-miR-222-3p, hsa-miR-222-5p, hsa-miR-223-3p, hsa-miR-223-5p, hsa-miR-23a-3p, hsa-miR-23a-5p, hsa-miR-23b-3p, hsa-miR-24-1-5p, hsa-miR-25-3p, hsa-miR-25-5p, hsa-miR-26a-1-3p, hsa-miR-26a-2-3p, hsa-miR-26a-5p, hsa-miR-26b-5p, hsa-miR-27a-3p, hsa-miR-27a-5p, hsa-miR-27b-3p, hsa-miR-27b-5p, hsa-miR-28-3p, hsa-miR-28-5p, hsa-miR-296-3p, hsa-miR-296-5p, hsa-miR-299-3p, hsa-miR-299-5p, hsa-miR-29a-3p, hsa-miR-29a-5p, hsa-miR-29b-1-5p, hsa-miR-29b-3p, hsa-miR-29c-3p, hsa-miR-301a-3p, hsa-miR-301a-5p, hsa-miR-301b-3p, hsa-miR-301b-5p, hsa-miR-302a-3p, hsa-miR-302a-5p, hsa-miR-302b-5p, hsa-miR-302c-3p, hsa-miR-302c-5p, hsa-miR-3065-3p, hsa-miR-3065-5p, hsa-miR-3074-3p, hsa-miR-3074-5p, hsa-miR-30a-3p, hsa-miR-30a-5p, hsa-miR-30b-3p, hsa-miR-30b-5p, hsa-miR-30c-1-3p, hsa-miR-30c-2-3p, hsa-miR-30c-5p, hsa-miR-30d-3p, hsa-miR-30d-5p, hsa-miR-30e-3p, hsa-miR-30e-5p, hsa-miR-31-3p, hsa-miR-31-5p, hsa-miR-3130-3p, hsa-miR-3130-5p, hsa-miR-3140-3p, hsa-miR-3140-5p, hsa-miR-3144-3p, hsa-miR-3144-5p, hsa-miR-3158-3p, hsa-miR-3158-5p, hsa-miR-32-3p, hsa-miR-32-5p, hsa-miR-320a, hsa-miR-323a-3p, hsa-miR-323a-5p, hsa-miR-324-3p, hsa-miR-324-5p, hsa-miR-326, hsa-miR-328-3p, hsa-miR-328-5p, hsa-miR-329-3p, hsa-miR-329-5p, hsa-miR-330-3p, hsa-miR-330-5p, hsa-miR-331-3p, hsa-miR-331-5p, hsa-miR-335-3p, hsa-miR-335-5p, hsa-miR-337-3p, hsa-miR-337-5p, hsa-miR-338-3p, hsa-miR-338-5p, hsa-miR-339-3p, hsa-miR-339-5p, hsa-miR-33a-3p, hsa-miR-33a-5p, hsa-miR-33b-3p, hsa-miR-33b-5p, hsa-miR-340-3p, hsa-miR-340-5p, hsa-miR-342-3p, hsa-miR-342-5p, hsa-miR-345-3p, hsa-miR-345-5p, hsa-miR-34a-3p, hsa-miR-34a-5p, hsa-miR-34b-3p, hsa-miR-34b-5p, hsa-miR-34c-3p, hsa-miR-34c-5p, hsa-miR-3605-3p, hsa-miR-3605-5p, hsa-miR-361-3p, hsa-miR-361-5p, hsa-miR-3613-3p, hsa-miR-3613-5p, hsa-miR-3614-3p, hsa-miR-3614-5p, hsa-miR-362-3p, hsa-miR-362-5p, hsa-miR-363-3p, hsa-miR-363-5p, hsa-miR-365a-3p, hsa-miR-365a-5p, hsa-miR-365b-3p, hsa-miR-365b-5p, hsa-miR-369-3p, hsa-miR-369-5p, hsa-miR-370-3p, hsa-miR-370-5p, hsa-miR-374a-3p, hsa-miR-374a-5p, hsa-miR-374b-3p, hsa-miR-374b-5p, hsa-miR-375, hsa-miR-376a-2-5p, hsa-miR-376a-3p, hsa-miR-376a-5p, hsa-miR-376c-3p, hsa-miR-376c-5p, hsa-miR-377-3p, hsa-miR-377-5p, hsa-miR-378a-3p, hsa-miR-378a-5p, hsa-miR-379-3p, hsa-miR-379-5p, hsa-miR-381-3p, hsa-miR-381-5p, hsa-miR-382-3p, hsa-miR-382-5p, hsa-miR-409-3p, hsa-miR-409-5p, hsa-miR-411-3p, hsa-miR-411-5p, hsa-miR-412-3p, hsa-miR-421, hsa-miR-423-3p, hsa-miR-423-5p, hsa-miR-424-3p, hsa-miR-424-5p, hsa-miR-425-3p, hsa-miR-425-5p, hsa-miR-431-3p, hsa-miR-431-5p, hsa-miR-432-5p, hsa-miR-433-3p, hsa-miR-433-5p, hsa-miR-449a, hsa-miR-449b-5p, hsa-miR-450a-1-3p, hsa-miR-450a-2-3p, hsa-miR-450a-5p, hsa-miR-450b-3p, hsa-miR-450b-5p, hsa-miR-451a, hsa-miR-452-3p, hsa-miR-4524a-3p, hsa-miR-4524a-5p, hsa-miR-4536-3p, hsa-miR-4536-5p, hsa-miR-454-3p, hsa-miR-454-5p, hsa-miR-4707-3p, hsa-miR-4707-5p, hsa-miR-4755-3p, hsa-miR-4755-5p, hsa-miR-4787-3p, hsa-miR-4787-5p, hsa-miR-483-3p, hsa-miR-483-5p, hsa-miR-484, hsa-miR-485-3p, hsa-miR-485-5p, hsa-miR-487b-3p, hsa-miR-487b-5p, hsa-miR-488-3p, hsa-miR-488-5p, hsa-miR-489-3p, hsa-miR-490-3p, hsa-miR-490-5p, hsa-miR-491-3p, hsa-miR-491-5p, hsa-miR-493-3p, hsa-miR-493-5p, hsa-miR-494-3p, hsa-miR-494-5p, hsa-miR-495-3p, hsa-miR-495-5p, hsa-miR-497-3p, hsa-miR-497-5p, hsa-miR-498, hsa-miR-5001-3p, hsa-miR-5001-5p, hsa-miR-500a-3p, hsa-miR-500a-5p, hsa-miR-5010-3p, hsa-miR-5010-5p, hsa-miR-503-3p, hsa-miR-503-5p, hsa-miR-504-3p, hsa-miR-504-5p, hsa-miR-505-3p, hsa-miR-505-5p, hsa-miR-506-3p, hsa-miR-506-5p, hsa-miR-508-3p, hsa-miR-508-5p, hsa-miR-509-3-5p, hsa-miR-509-3p, hsa-miR-509-5p, hsa-miR-510-3p, hsa-miR-510-5p, hsa-miR-512-5p, hsa-miR-513c-3p, hsa-miR-513c-5p, hsa-miR-514a-3p, hsa-miR-514a-5p, hsa-miR-514b-3p, hsa-miR-514b-5p, hsa-miR-516b-5p, hsa-miR-518c-3p, hsa-miR-518f-3p, hsa-miR-5196-3p, hsa-miR-5196-5p, hsa-miR-519a-3p, hsa-miR-519a-5p, hsa-miR-519c-3p, hsa-miR-519e-3p, hsa-miR-520c-3p, hsa-miR-520f-3p, hsa-miR-520g-3p, hsa-miR-520h, hsa-miR-522-3p, hsa-miR-525-5p, hsa-miR-526b-5p, hsa-miR-532-3p, hsa-miR-532-5p, hsa-miR-539-3p, hsa-miR-539-5p, hsa-miR-542-3p, hsa-miR-542-5p, hsa-miR-543, hsa-miR-545-3p, hsa-miR-545-5p, hsa-miR-548a-3p, hsa-miR-548a-5p, hsa-miR-548ar-3p, hsa-miR-548ar-5p, hsa-miR-548b-3p, hsa-miR-548d-3p, hsa-miR-548d-5p, hsa-miR-548e-3p, hsa-miR-548e-5p, hsa-miR-548h-3p, hsa-miR-548h-5p, hsa-miR-548j-3p, hsa-miR-548j-5p, hsa-miR-548o-3p, hsa-miR-548o-5p, hsa-miR-548v, hsa-miR-551b-3p, hsa-miR-551b-5p, hsa-miR-552-3p, hsa-miR-556-3p, hsa-miR-556-5p, hsa-miR-561-3p, hsa-miR-561-5p, hsa-miR-562, hsa-miR-567, hsa-miR-569, hsa-miR-570-3p, hsa-miR-570-5p, hsa-miR-571, hsa-miR-574-3p, hsa-miR-574-5p, hsa-miR-576-3p, hsa-miR-576-5p, hsa-miR-577, hsa-miR-579-3p, hsa-miR-579-5p, hsa-miR-582-3p, hsa-miR-582-5p, hsa-miR-584-3p, hsa-miR-584-5p, hsa-miR-589-3p, hsa-miR-589-5p, hsa-miR-590-3p, hsa-miR-590-5p, hsa-miR-595, hsa-miR-606, hsa-miR-607, hsa-miR-610, hsa-miR-615-3p, hsa-miR-615-5p, hsa-miR-616-3p, hsa-miR-616-5p, hsa-miR-617, hsa-miR-619-5p, hsa-miR-624-3p, hsa-miR-624-5p, hsa-miR-625-3p, hsa-miR-625-5p, hsa-miR-627-3p, hsa-miR-627-5p, hsa-miR-628-3p, hsa-miR-628-5p, hsa-miR-629-3p, hsa-miR-629-5p, hsa-miR-630, hsa-miR-633, hsa-miR-634, hsa-miR-635, hsa-miR-636, hsa-miR-640, hsa-miR-642a-3p, hsa-miR-642a-5p, hsa-miR-643, hsa-miR-645, hsa-miR-648, hsa-miR-6503-3p, hsa-miR-6503-5p, hsa-miR-651-3p, hsa-miR-651-5p, hsa-miR-6511a-3p, hsa-miR-6511a-5p, hsa-miR-652-3p, hsa-miR-652-5p, hsa-miR-653-5p, hsa-miR-654-3p, hsa-miR-654-5p, hsa-miR-657, hsa-miR-659-3p, hsa-miR-660-3p, hsa-miR-660-5p, hsa-miR-664b-3p, hsa-miR-664b-5p, hsa-miR-671-3p, hsa-miR-671-5p, hsa-miR-675-3p, hsa-miR-675-5p, hsa-miR-7-1-3p, hsa-miR-7-5p, hsa-miR-708-3p, hsa-miR-708-5p, hsa-miR-744-3p, hsa-miR-744-5p, hsa-miR-758-3p, hsa-miR-758-5p, hsa-miR-765, hsa-miR-766-3p, hsa-miR-766-5p, hsa-miR-767-3p, hsa-miR-767-5p, hsa-miR-769-3p, hsa-miR-769-5p, hsa-miR-802, hsa-miR-873-3p, hsa-miR-873-5p, hsa-miR- 874-3p, hsa-miR-874-5p, hsa-miR-876-3p, hsa-miR-876-5p, hsa-miR-885-3p, hsa-miR-885-5p, hsa-miR-887-3p, hsa-miR-887-5p, hsa-miR-9-3p, hsa-miR-9-5p, hsa-miR-92a-1-5p, hsa-miR-92a-2-5p, hsa-miR-92a-3p, hsa-miR-92b-3p, hsa-miR-92b-5p, hsa-miR-93-3p, hsa-miR-93-5p, hsa-miR-941, hsa-miR-942-3p, hsa-miR-942-5p, hsa-miR-96-3p, hsa-miR-96-5p, hsa-miR-98-3p, hsa-miR-98-5p, hsa-miR-99a-3p, hsa-miR-99a-5p, hsa-miR-99b-3p, and hsa-miR-99b-5p.

An "output molecule," as used herein, refers to a signal produced by the engineered RNA carrier after detecting the presence, absence or the level of an input signal (e.g., the first miRNA). The miRNA based logic gate that comprises the engineered RNA carrier of the present disclosure is designed such that the output molecule (e.g., the second miRNA) is expressed when an input signal (e.g., the first miRNA) is absent. In some embodiments, the output molecule (e.g., the second miRNA) has a basal expression level and the expression level increases (e.g., by at least 20%) when the input signal (e.g., the first miRNA) is absent or when the expression level of the input signal (e.g., the first miRNA) deceases (e.g., by at least 20%), compared to when the input signal (e.g., the first miRNA) is present. For example, the expression level of the output molecule (e.g., the second miRNA) may be at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher when the input signal (e.g., the first miRNA) is absent or when the expression level of the input signal (e.g., the first miRNA) deceases (e.g., by at least 20%), compared to when the input signal (e.g., the first miRNA) is present or when the expression level of the input signal (e.g., the first miRNA) increases (e.g., by at least 20%). In some embodiments, the expression level of the output molecule (e.g., the second miRNA) is 20%, 30%, 40%, 50%, 60%, 70%, 80%, 90%, 100%, 2-fold, 5-fold, 10-fold, 100-fold, 1000-fold, or higher when the input signal (e.g., the first miRNA) is absent or when the expression level of the input signal (e.g., the first miRNA) deceases (e.g., by at least 20%), compared to when the input signal (e.g., the first miRNA) is absent or when the expression level of the input signal (e.g., the first miRNA) deceases (e.g., by at least 20%).

In some embodiments, the output molecule (e.g., the second miRNA) is a therapeutic RNA interference (RNAi) molecule (e.g., a microRNA, siRNA, or shRNA) or a nucleic acid enzyme (e.g., a ribozyme). RNAi molecules and their use in silencing gene expression are familiar to those skilled in the art. In some embodiments, the therapeutic RNAi molecule is a therapeutic miRNA. Non-limiting examples of therapeutic miRNAs have been described in the art, see e.g., Chakraborty, Therapeutic miRNA and siRNA: Moving from Bench to Clinic as Next Generation Medicine, Molecular Therapy Nucleic Acids, Review| Volume 8, P132-143, Sep. 15, 2017.

RNA fragments with free and unprotected 3' ends (in the 5' fragment) and 5' ends (in the 3' fragment) are generated upon cleavage, which are rapid degraded if unprotected. In some embodiments, the engineered RNA carrier further comprises a 3' cap. Non-limiting examples of 3' cap: synthetic poly-adenylated tails, and stabilizing RNA triple helix structures such as MALAT1 (e.g., as described in Brown et al., Nature Structural & Molecular Biology 21, 633-640, 2014, incorporated herein by reference), MENßenB triplex, HSHV PAN triplex, and histone stem loop.

Also within the scope of the present disclosure is an engineered nucleic acid that encodes the miRNA based logic gate. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., Green and Sambrook, Molecular Cloning, A Laboratory Manual, 2012, Cold Spring Harbor Press). In some embodiments, the miRNA based NOT gate may be included in one or more (e.g., 2, 3, 4, 5, 6, 7, 8, 9, 10, or more) nucleic acid molecules (e.g., vectors) and introduced into a cell.

In some embodiments, the engineered nucleic acid comprises a promoter operably linked to a nucleotide sequence encoding the miRNA based logic gate. A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof. A promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a nucleic acid sequence may be positioned under the control of a recombinant or heterologous promoter, which refers to a promoter that is not normally associated with the encoded sequence in its natural environment. such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202, 5,928,906).

In some embodiments, a promoter is a constitutive promoter. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is a U6 promoter.

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter. An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

Also within the scope of the present disclosure are cells comprising the miRNA based logic gate and the engineered nucleic acid encoding the same described herein. The cell can be any cell suitable for expressing the miR-based logic gate. In some embodiments, the cells are prokaryotic cells. In some embodiments, the cells are bacteria cells. In other embodiments, the cells are eukaryotic cells. In some embodiments, the cells are mammalian cells. In other examples, the cells are human cells or non-human cells. Non-limiting example for non-human cells can be non-human mammalian cells, plant cells, insect cells, bacterial cells or fungi cells. In some embodiments, the cell is a specific cell type in tissue. In some embodiments, the cell is a specific diseased cell. In some embodiments, the cell expresses the first miRNA and does not express the second miRNA. In some embodiments, the cell does not expresses the first miRNA and express the second miRNA. In some embodiments, the cell expresses both the first and the second miRNA, and the downregulation of the first miRNA leads to the upregulation of the second miRNA. In some embodiments, the cell expresses both the first and the second miRNA, and the upregulation of the first miRNA leads to the downregulation of the second miRNA. non-limiting examples of the tissues are lung tissue, skin tissue, breast tissue, connective tissue, brain tissue, gastrointestinal tissue, heart tissue, kidney tissue, etc. non-limiting examples for specific cell types are epithelial cells, endothelial cells, fibroblasts, immune cells, etc. non-limiting examples of a diseased cells are neo-plastic cells, infected cells, cells harboring genetic mutations, fibro genetic cells, etc. The miR-based logic gate, the engineered nucleic acid and/or the vectors can be delivered to the cells by methods known in the art. Non-limiting methods of delivery is transfection (e.g., electroporation, or liposome), viral particles (e.g., adeno-associated virus), nanoparticles (e.g., lipid nanoparticles), or genomic integration. In some embodiments, the engineered nucleic acid described herein is integrated into the genomic DNA of the cell. Genomic integration of the present engineered nucleic acid can be done by methods known in the art. In some embodiments, the genomic integration of the present engineered nucleic acid can be achieved by viral transduction (e.g., including but not limited to lentiviral vectors, retroviral vectors, piggybac transposon vector and sleepingbeauty transposon vector) and introduced into host immune cells using conventional recombinant technology. Sambrook et al., Molecular Cloning, A Laboratory Manual, 3rd ed., Cold Spring Harbor Laboratory Press.

Also provided herein are organisms comprising the miR based logic gate, the engineered nucleic acid encoding the same, the vector and/or cells described herein.

Exemplary organisms can be prokaryotic organisms or eukaryotic organisms. In some embodiments, the prokaryotic organism is a bacteria. In some embodiments, the eukaryotic organism is an animal, a plant, or a fungus. In some embodiments, the eukaryotic organism is an animal. In some further examples, the animal is a non-human animal. Non-limiting examples of non-human animals are mice, chickens, goats, rabbits, pigs, donkeys, cows, or camels.

II. Recombinant Viruses for Delivery of the miRNA Logic Gate

Also within the scope of the present disclosure are the delivery of the engineered nucleic acid encoding the miR based logic gate by recombinant viruses. Non-limiting examples of such recombinant viruses are adeno-associated viruses, lentivirus, alphavirus, adeno virus, or bacterial phage.

In some embodiments, the engineered nucleic acid encoding the miR based logic gate are delivered by adeno-associated viruses (AAV). The engineered nucleic acid encoding the miR based logic gate may be recombinant adeno-associated virus (AAV) vectors (rAAV vectors). In some embodiments, an engineered nucleic acid encoding the miR based logic gate as described by the disclosure comprises a first adeno-associated virus (AAV) inverted terminal repeat (ITR) and a second AAV ITR, or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The miR based logic gate coding sequence may also comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the miR based logic gate coding sequence, in which the selected the miR based logic gate coding sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; and when desired, sequences that enhance secretion of the encoded product. A number of expression control sequences, including promoters which are native, constitutive, inducible and/or tissue-specific, are known in the art and may be utilized. In some embodiments, the miR based logic gate coding sequence is operably linked to a suitable promoter described herein above.

In some aspects, the disclosure provides isolated AAVs (e.g., rAAVs encoding the miR-based logic gate). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. In some embodiments, an rAAV expressing the miR-based logic gate is capable of increasing tissue or cell specificity such that the miR-based logic gate can only function in the cells having the intended miR biomarker signature that the rAAV can infect.

Methods for obtaining recombinant AAVs (e.g., encoding the miR-based logic gate) having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, the rAAV (e.g., encoding the miR-based logic gate) comprises an AAV capsid protein is of an AAV serotype selected from the group consisting of AAV2, AAV3, AAV4, AAV5, AAV6, AAV8, AAVrh8, AAV9, and AAV10.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. see, e.g., k. fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells. A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

In some embodiments, an rAAV described herein (e.g., encoding the miR-based logic gate) is a single stranded rAAV. An ssAAV, as used herein, refers to a rAAV with the coding sequence and complementary sequence of the transgene expression cassette on separate strands and are packaged in separate viral capsids. In some embodiments, the rAAV (e.g., encoding the miR-based logic gate) is a self-complementary AAV (scAAV). A scAAV, as used herein, refers to an rAAV with both the coding and complementary sequence of the transgene expression cassette are present on each plus-and minus-strand genome. The coding region of a scAAV was designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription.

III. Pharmaceutical Compositions

In some aspects, the present disclosure, at least in part, relates to a pharmaceutical composition, comprising the miRNA based logic gate, the engineered nucleic acid, the recombinant virus, the cells, as described herein. The pharmaceutical composition described herein may further comprise a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used for in vivo administration must be sterile. This is readily accomplished by, for example, filtration through sterile filtration membranes. The pharmaceutical compositions described herein may be placed into a container having a sterile access port, for example, an intravenous solution bag or vial having a stopper pierceable by a hypodermic injection needle.

In other embodiments, the pharmaceutical compositions described herein can be formulated for intra-muscular injection, intravenous injection, intratumoral injection or subcutaneous injection.

The pharmaceutical compositions described herein to be used in the present methods can comprise pharmaceutically acceptable carriers, buffer agents, excipients, salts, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises lipid nanoparticles which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In other examples, the pharmaceutical composition described herein can be formulated in sustained-release format. Suitable examples of sustained-release preparations include semipermeable matrices of solid hydrophobic polymers containing the miR-based logic gate, the nucleic acid encoding the same, the recombinant virus encoding the same or the cell comprising the same, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

Suitable surface-active agents include, in particular, non-ionic agents, such as polyoxyethylenesorbitans (e.g., TWEEN™ 20, 40, 60, 80 or 85) and other sorbitans (e.g., SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets having a suitable size and can have a pH in the range of 5.5 to 8.0.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

IV. Therapeutic Applications

The miRNA based logic gate, the engineered nucleic acid, the recombinant virus, the cells and the pharmaceutical composition described herein, can be used to treat various diseases (e.g., diseases cell having the correct miRNA biomarker signature, and can be targeted the miRNA to be expressed by the miRNA based logic gate).

To practice the method disclosed herein, an effective amount of any of the pharmaceutical compositions described herein can be administered to a subject (e.g., a human) in need of the treatment via a suitable route, such as intratumoral administration, by intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, pharmaceutical composition described herein can be aerosolized using a fluorocarbon formulation and a metered dose inhaler, or inhaled as a lyophilized and milled powder. In some examples, the pharmaceutical composition described herein is formulated for intratumoral injection. In particular examples, the pharmaceutical composition may be administered to a subject (e.g., a human patient) via a local route, for example, injected to a local site such as a tumor site or an infectious site.

As used herein, "an effective amount" refers to the amount of each active agent required to confer therapeutic effect on the subject, either alone or in combination with one or more other active agents. For example, the therapeutic effect can be reduced tumor burden, reduction of cancer cells, increased immune activity, reduction of a mutated protein, reduction of over-active immune response. Determination of whether an amount of miR-based logic gate achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of pharmaceutical composition described herein may be appropriate. Various formulations and devices for achieving sustained release are known in the art.

In some embodiments, the treatment is a single injection of the s pharmaceutical composition described herein. In some embodiments, the method described herein comprises administering to a subject in need of the treatment (e.g., a human patient) one or multiple doses of pharmaceutical composition described herein.

In some example, dosages for a pharmaceutical composition described herein may be determined empirically in individuals who have been given one or more administration(s) of the pharmaceutical composition. Individuals are given incremental dosages of the synthetic pharmaceutical composition described herein. To assess efficacy of the miRNA-based logic gate, an indicator of the disease/disorder can be followed. For repeated administrations over several days or longer, depending on the condition, the treatment is sustained until a desired suppression of symptoms occurs or until sufficient therapeutic levels are achieved to alleviate a target disease or disorder, or a symptom thereof.

In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen of the pharmaceutical composition described herein used can vary over time.

For the purpose of the present disclosure, the appropriate dosage of the pharmaceutical composition described herein will depend on the specific miRNA signature of the cell and the miRNA to be expressed, the type and severity of the disease/disorder, the pharmaceutical composition described herein is administered for preventive or therapeutic purposes, previous therapy, the patient's clinical history and response to the miRNA based logic gate, and the discretion of the attending physician. A clinician may administer a pharmaceutical composition described herein, until a dosage is reached that achieves the desired result. Methods of determining whether a dosage resulted in the desired result would be evident to one of skill in the art. Administration of one or more pharmaceutical composition described herein can be continuous or intermittent, depending, for example, upon the recipient's physiological condition, whether the purpose of the administration is therapeutic or prophylactic, and other factors known to skilled practitioners. The administration pharmaceutical composition described herein may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

The subject to be treated by the methods described herein can be a mammal, such as a human, farm animals, sport animals, pets, primates, horses, dogs, cats, mice and rats. In one embodiment, the subject is a human.

In some embodiments, the subject may be a human patient having, suspected of having, or at risk for a disease. Non-limiting examples of diseases that are suitable for miR based therapy are: Alpha-1 antitrypsin deficiency, Hypercholesterolemia, Hepatitis B infection, Liver adenoma due to HIV infection, Hepatitis C virus infection, Ornithine transcarbamylase deficiency, Hepatocellular carcinoma, Amyotrophic lateral sclerosis, Spinocerebellar ataxia type 1, Huntington's disease, Parkinson disease, Spinal and Bulbar muscular atrophy, Pyruvate dehydrogenase deficiency, Hyperplasia, obesity, facioscapulohumeral muscular dystrophy (FSHD), Nerve Injury-induced Neuropathic Pain, Age-related macular degeneration, Retinitis pigmentosa, heart failure, cardiomyopathy, cold-induced cardiovascular dysfunction, Asthma, Duchenne muscular dystrophy, infectious diseases, or cancer.

Non limiting examples of cancers include melanoma, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, prostate cancer, vulval cancer, thyroid cancer, hepatic carcinoma, gastric cancer, and various types of head and neck cancer, including squamous cell head and neck cancer. In some embodiments, the cancer can be melanoma, lung cancer, colorectal cancer, renal-cell cancer, urothelial carcinoma, or Hodgkin's lymphoma.

A subject having a target disease or disorder (e.g., cancer or an infectious disease) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

In some embodiments, a pharmaceutical composition described herein may be co-used with another suitable therapeutic agent (e.g., an anti-cancer agent an anti-viral agent, or an anti-bacterial agent) and/or other agents that serve to enhance effect of a miRNA based NOT gate. In such combined therapy, the pharmaceutical composition described herein, and the additional therapeutic agent (e.g., an anti-cancer therapeutic agent or others described herein) may be administered to a subject in need of the treatment in a sequential manner, i.e., each therapeutic agent is administered at a different time. Alternatively, these therapeutic agents, or at least two of the agents, are administered to the subject in a substantially simultaneous manner. Combination therapy can also embrace the administration of the agents described herein in further combination with other biologically active ingredients (e.g., a different anti-cancer agent) and non-drug therapies (e.g., surgery).

V. General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A laboratory notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: State of Art miRNA-Based NOT Gate that Requires Exogenous Proteins

Due to the relevance of miRNAs in cell state and line biomarker signatures and the possibility to engineer them to tune the gene expression of any coding gene of choice, there currently is a growing and pressing need to engineer genetic circuits that allow a therapeutic miRNA agent to be expressed according to a certain miRNAs signature without the use of exogenous proteins. Because of this, an investigation of ways to engineer miRNAs that are downregulated by miRNAs without the use of exogenous proteins was started. These genetic devices are referred to as NOT-gate, where the downregulated miRNA is the output of the gate and the downregulating miRNA is the input.

Such NOT-gate has a terrific potential for two reasons. First, it can be directly used in all gene therapies where just a miRNA is delivered to cells. The possibility to turn ON and OFF the miRNA therapeutic agent according to a miRNA signature would reduce the unwanted side effects of those therapies without adding the risk of dangerous immune reactions. Second, a NOT-gate where the input and output are both miRNAs can easily be the building block of more sophisticated computations in mammalian cells.

Figure 6A:
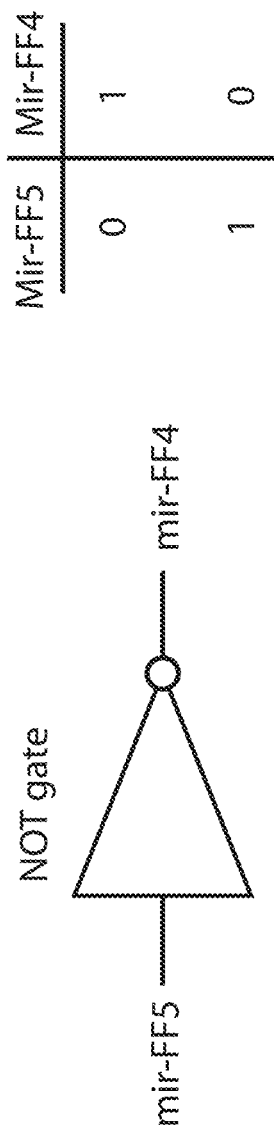
FIGS. 6A-6E show scaling up of miRNA-based logic-gates. Sophisticated logic circuits require a large design space. Watson and Crick base pairs provide this design space. A miRNA based NOT gate can be engineered, because miRNA recognizes its target by Watson and Crick base pairs. This allows the design of orthogonal signals.
Figure 6B:
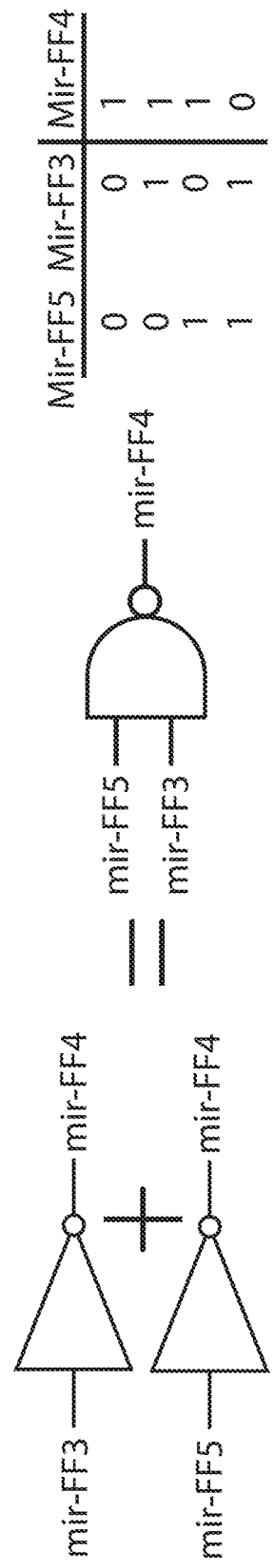
Figure 6C:
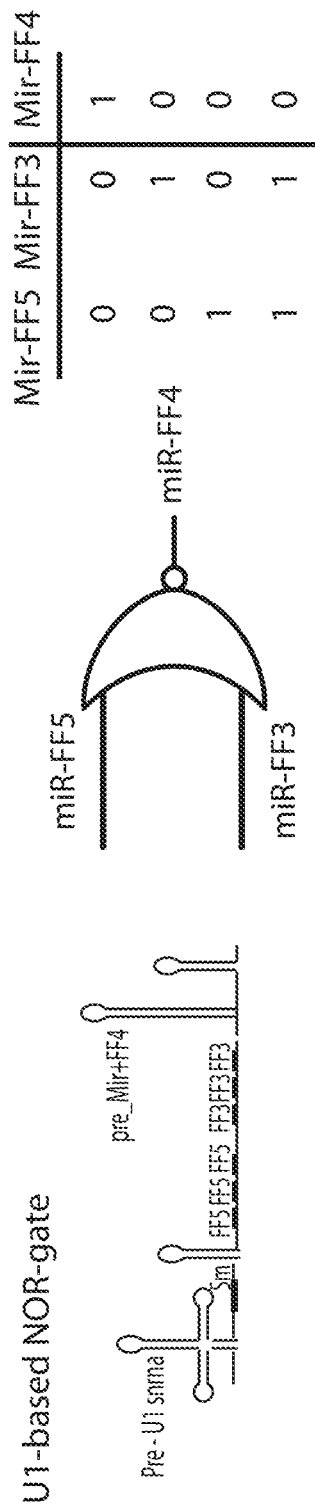

The Watson and Crick base pairing is the mechanism that allows the RISC complex to identify the target RNA to be downregulated. This mechanism provides a large design space which in turn allows the design of many NOT-gates with signal orthogonal to each other. For instance, two gates together form a NAND gate, two NAND gates form a flip flop, and an odd number of NOT gates in cascade form an oscillator (FIGS. 6A-6C).

The research article "Efficient Detection and Purification of Cell Populations Using Synthetic MicroRNA Switches." Cell Stem Cell 16, 699-711 (2015) classifies cell lines, but it does not provide regulation of miRNA expression. Instead, the miRNA based NOT-gate, which here is disclosed, is the only available technology to provide such regulation without the use of exogenous proteins and with just one transcriptional unit for a small DNA footprint.

To investigate ways for the engineering of a miRNA-based NOT-gate that does not use exogenous proteins, how to engineer a miRNA-based NOT-gate, according to the current state of the art, was analyzed.

Figure 1A:
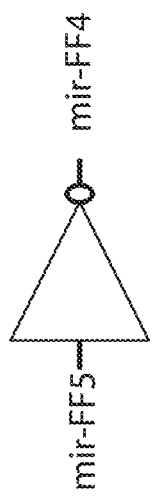
FIG. 1A shows a NOT-gate where the input is mirFF5 and the output is mirFF4.
Figure 1B:
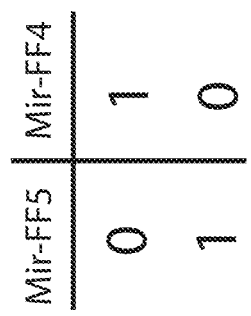
FIG. 1B shows a truth-table of the NOT-gate in FIG. 1A.

As described above, most of the miRNA based genetic circuit requires the use of exogenous proteins, as illustrated in FIGS. 1A-1C. In FIG. 1A, the symbol of a NOT gate where the input is mirFF5 and the output is mirFF4 is shown. FIG. 1B shows the table of truth of the NOT gate. FIG. 1C shows an example of how a NOT gate could be engineered according to the current state of the art.

A protein activator is expressed if and only if the mirFF5 is not expressed. As consequence, when mirFF5 is not expressed, the activator and the mirFF4 is expressed. On the other hand, when mirFF5 is expressed, the activator is downregulated and so the mirff4 is not expressed (mirFF4 and mirFF5 are miRNAs orthogonal to each other; any other orthogonal miRNAs can be used instead of mirFF4 and mirFF5). While this is definitely a NOT-gate behavior, unfortunately, the use of the activator protein, which is an exogenous protein, makes this design not suitable for gene therapy because of the risk of immunogenicity.

The analysis of the design shown in FIG. 1C did not provide any insight on how to design a miRNA-based NOT-gate that does not use exogenous proteins.

Figure 1D:
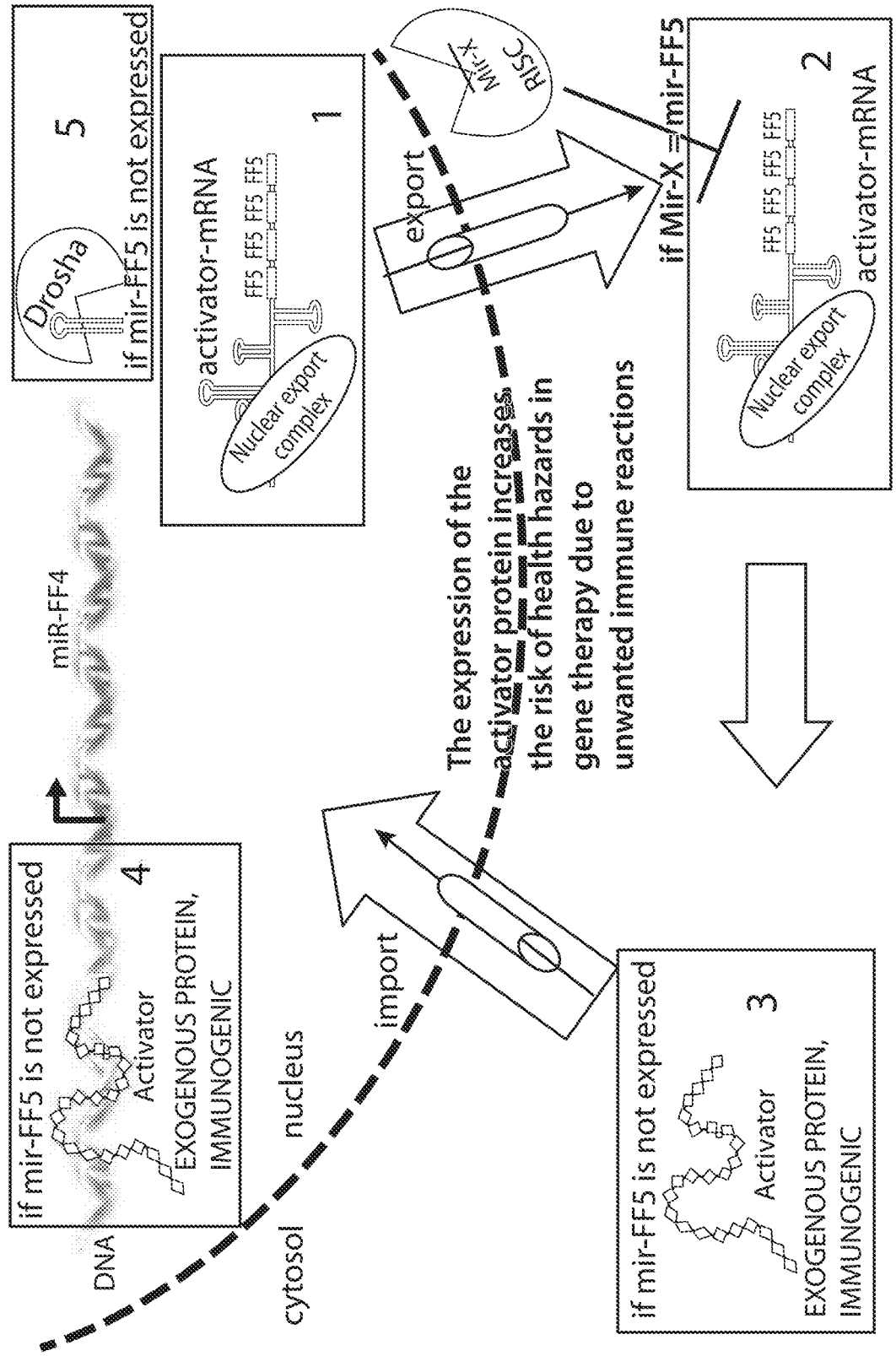
FIG. 1D is a diagram showing how miRNA-based NOT-gate that requires an exogenous protein functions, and that the expression of the activator protein increases the risk of health hazards in gene therapy due to the unwanted immune reaction to the exogenous protein.

As consequence the behavior at a biomolecular level of a miRNA-based NOT-gate was thoroughly analyzed (FIG. 1D).

Here, after the mRNA of the activator is transcribed (FIG. 1D, part 1), it is exported from the nucleus to the cytosol (FIG. 1D, part 2). Then, if mirFF5 is not expressed, the mRNA is translated into a protein (FIG. 1D, part 3), which in turn is brought back to the nucleus where it can activate the transcription of the mirFF4 (FIG. 1D, part 4). Finally, Drosha can process the pre-mirFF4 to start the miRNA biogenesis.

Example 2: Design of a miRNA-Based NOT Gate that Does not Require Exogenous Proteins by Using An Engineered RNA Carrier There are two important things to note with the above analysis. First, the role of the mRNA in this design was to probe the presence of the mirFF5 in the cytosol. Second, the role of the activator protein was simply to bring back to the nucleus the information that the mirFF5 was not expressed in the cytosol. Overall, there were two different biomolecules, an mRNA and a protein, that implemented these two roles.

This insight triggered the idea to investigate whether these two roles could be implemented by just one molecule instead of two. Furthermore, because it is not desirable to use exogenous proteins to facilitate the functions of the miR-based NOT gate, an investigation on whether just a single non-coding RNA, with potential for both roles, without using any exogenous protein was started. This RNA was referred to as RNA-carrier.

Figure 3:
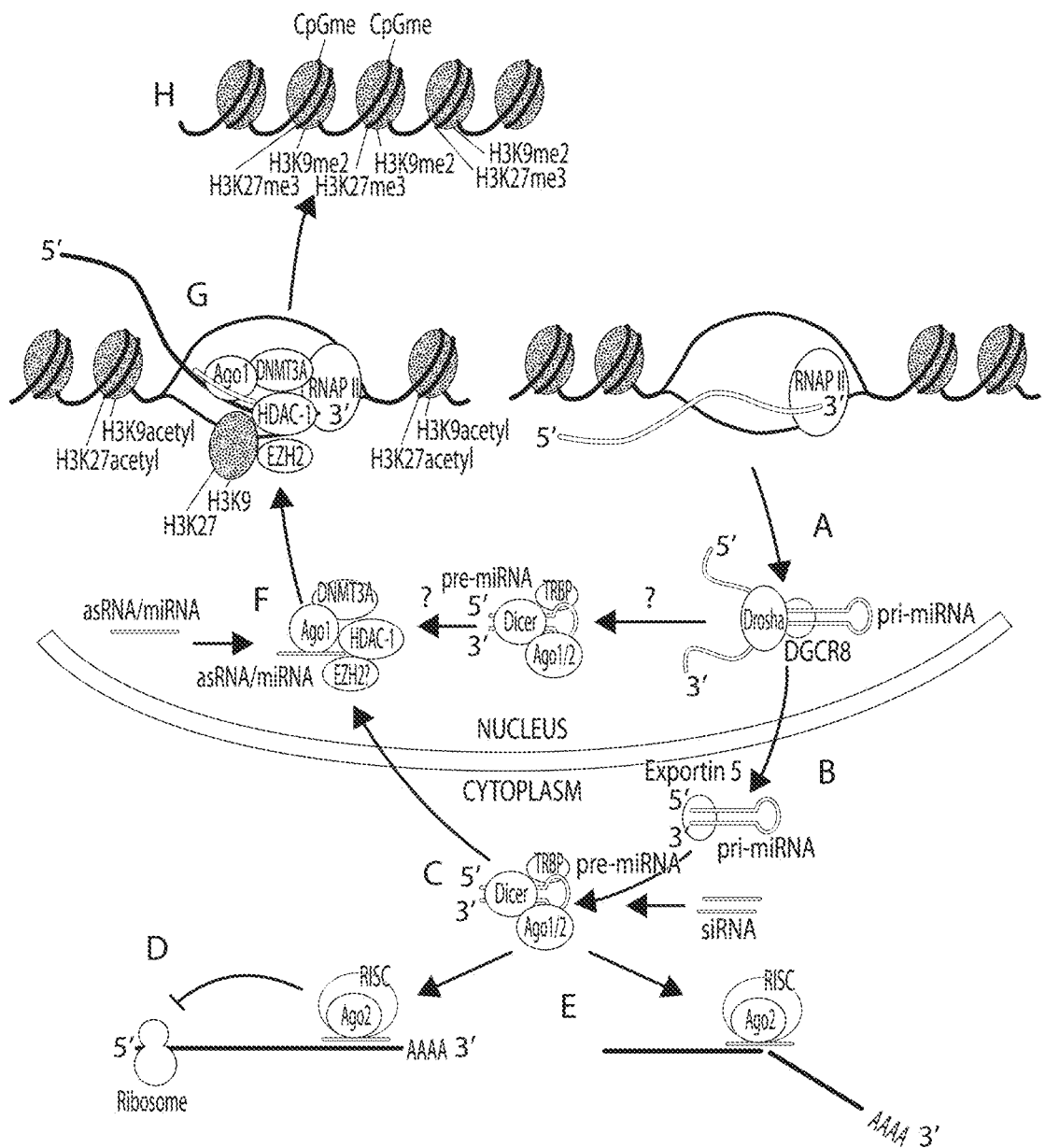
FIG. 3 is a diagram showing transcriptional gene silencing in human nucleic acids research. There can be ncRNAs that are localized close to transcriptional regulators sites on the genome. Some of these ncRNAs can be regulated by Ago1, and it appears that they do NOT shuttle between the nucleus and the cytosol being predominately nuclear. In order to be a possible candidate as an RNA-carrier, in addition of being regulated by Ago1, it should also have the ability to regulate in turn transcription; these ncRNAs appear to be involved in epigenetic silencing.

More importantly, an RNA-carrier can be used to implement a NOT gate, but this is not restricted to post-transcriptional silencing downregulation nor the RNA carrier is restricted in being shuttled between the nucleus and the cytosol. Indeed, because a miRNA can be biologically active either through Ago1 or Ago2 complexes, Aan RNA, in order to be a candidate as RNA-carrier, necessarily has to be shuttled back and forth between a region of the cell where it can be either targeted by either Ago1 (in the nucleus) or Ago2 (in the cytosol) to a region of the cell where it can either start directly the miRNA biogenesis or regulate transcription (FIG. 3). In this latter case, an RNA-carrier can tune the transcription of an RNA (either coding or non-coding) according to an miRNA signature without comprising a pre-miRNA sequence (the second miRNA).

Figure 2:
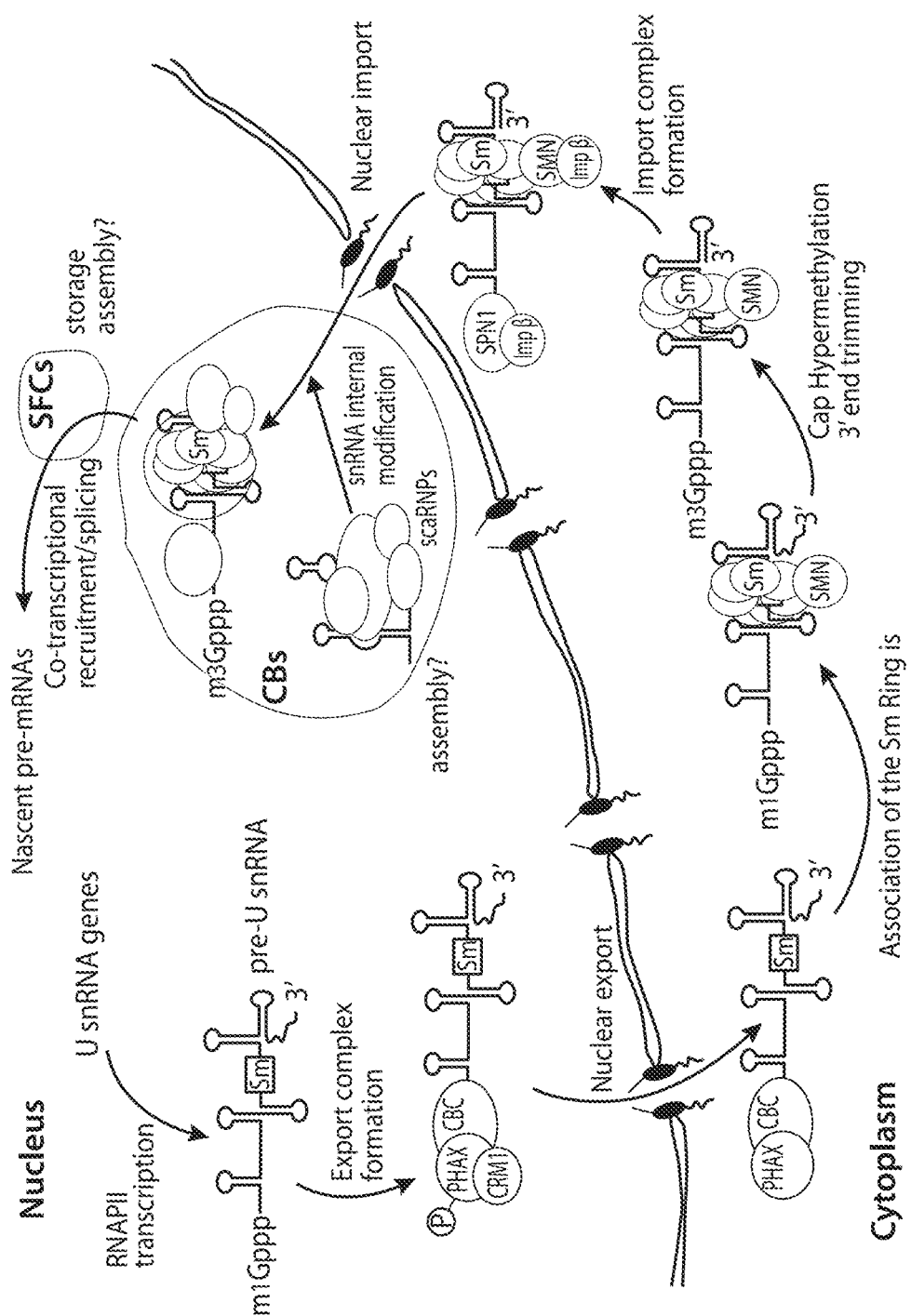
FIG. 2 is a diagram showing the assembly of a spliceosomal small nuclear ribonucleoprotein particle. The U snRNA genes are non-coding RNAs involved in the spliceosome. The biogenesis of all U snRNA except the U6 requires a passage from the nucleus to the cytosol and back into the nucleus. Key steps in U snRNA biogenesis is the transport to the cytosol after transcription, binding of the SMN complex, binding of the SM proteins, and finally the shuttling back to the nucleus. The U snRNAs represent a subset of possible RNA-carriers. Being shuttled back and forth from the nucleus to the cytoplasm is not a necessary condition to be a RNA-carrier.

Here, ncRNA that were able to shuttle back and forth between, but not limited to, the nucleus and the cytosol were tested. After an extensive investigation in literature, it was discovered that the U snRNA genes, which are involved in the spliceosome, are indeed naturally shuttled back and forth from the nucleus to the cytosol (FIG. 2). Key steps in their biogenesis are their transport to the cytosol after transcription, the binding of the SMN complex, the binding of the SM proteins, and then the shuttling back to the nucleus. The U1 snRNA was used as a carrier.

In the following, the implementation of the general idea where the RNA-carrier is the U1 snRNA and where the absence of a specific miRNA biomarker triggers in a living cell the expression of another miRNA is explained. The U1 snRNA gene is naturally shuttled back and forth from the nucleus to the cytosol. Because of this, a new U1 snRNA was designed by adding to the endogenous RNA sequence in addition to the RNA sequences that encode both mir-FF5 target sites and a pre-miRNA sequence for mir-FF4. These target sites define the input of the NOT gate and the pre-micro-RNA FF4, which in turn defines the output (as mentioned, mir-FF4 and mir-FF5 are two micro-RNAs, orthogonal with each other) (FIGS. 4A-4C).

Assuming that the insertion of the exogenous RNA sequence would not disrupt the U1 snRNA biogenesis, when such U1 is transcribed (FIG. 4D, part 1) it should be exported to the cytosol (FIG. 4D, part 2), then the SMN complex and the SM proteins should bind to it (FIG. 4D, part 3) and finally, if the mir-FF5 is not expressed such that the modified U1 snRNA is destroyed, the entire U1 complex should be brought into the nucleus. There, the Drosha could process the pre-mir-FF4 (FIG. 4D, part 4) which in turn would lead to the expression of the mir-FF4 in the cytosol.

When instead the mir-FF5 is expressed, the RISC-mir-FF5 would target the modified U1 snRNA and consequently the pre-mir-FF4 would not reach the nucleus. Because the Drosha operates in the nucleus and the RISC is not able to directly process the pre-micro-RNA in the cytosol, there would be no expression of mir-FF4. This would lead to a NOT-gate behavior, which, of course, can be replicated with miRNAs other than mir-FF4 and mir-FF5.

Figure 4D:
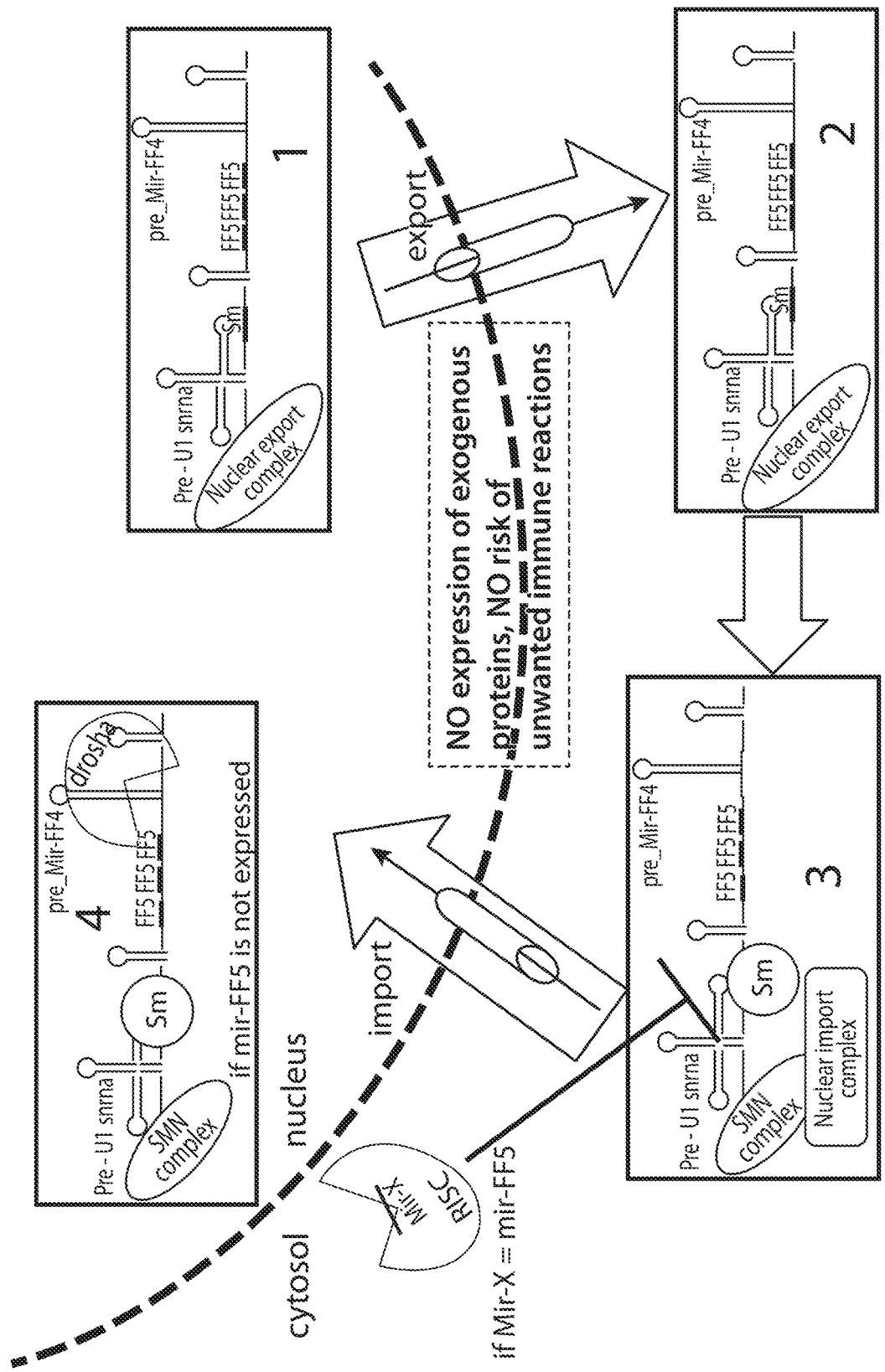

More importantly, this mechanism also would not depend on whether the RISC acts on the U1 soon after it arrives in the cytosol (FIG. 4D, part 2) or after the binding of the MSM and SM proteins (FIG. 4D, part 3). In addition, there would still be a NOT-gate behavior in case the targeting on the U1 snRNA happens trough Argo1 instead of Argo2.

Figure 5C:
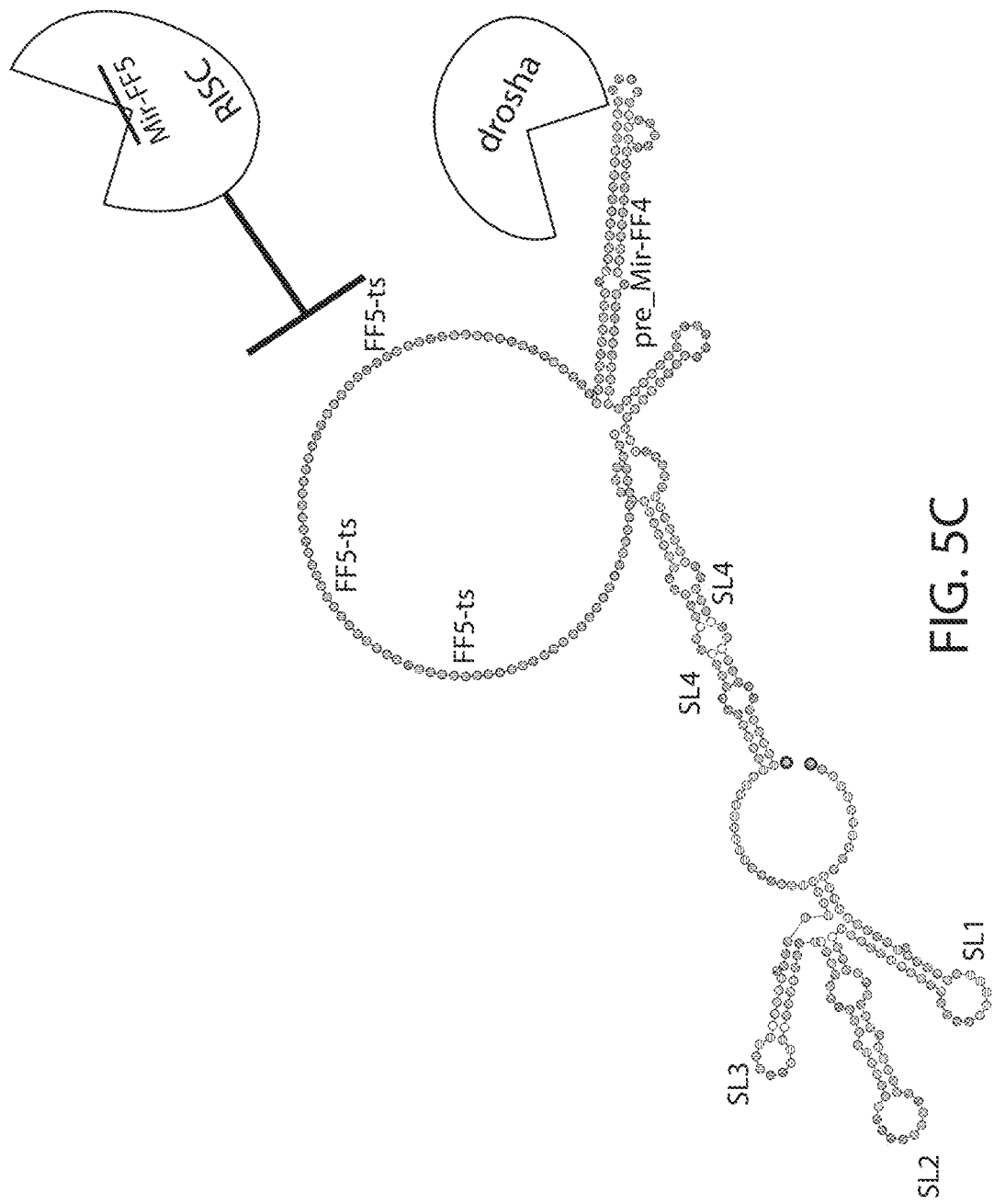

Once the U1 snRNA NOT gate was designed (as shown in FIGS. 5A-5C), and an extensive literature research was completed prior to testing in an effort to check whether that design would work. As consequence of that literature research, it was important to highlight that the current scientific knowledge could not predict whether this design was going to be successful or not for the following reasons:

First, the current scientific knowledge could not predict whether the modified U1 snRNA (the one that implements the NOT-gate by the insertion of the exogenous RNA sequence) was short enough to avoid the transportation from the nucleus to the cytosol through the mRNA pathway. Had that transportation taken place, that NOT-gate design would have failed. Secondly, it could not predict whether Drosha was going to completely process the pre-miRNA before the export of the U1 snRNA to the cytosol. Had Drosha completely processed the pre-miRNA before that export, the NOT-gate design would have failed. Third, it could not predict whether the RISC-complex could target the U snRNAs. Had the RISC not been able to target the U1, the NOT-gate design would have failed. Fourth, it could not predict whether Drosha could process the pre-miRNA after the import from the cytosol to the nucleus. Had Drosha not been able to process the pre-miRNA after that import, the NOT-gate design would have failed. Fifth, it could not predict whether the insertion of that exogenous RNA sequence in the U1 was going to impede the binding of endogenous proteins involved in the shuttling of the U1. Again, had that insertion impeded the binding of critical proteins in the U1 biogenesis, the NOT-gate design would have failed. Lastly, it could not predict whether the pre-miRNA added to the U1 was going to be degraded in the cytosol. Also in this case, had the pre-miRNA been degraded, that NOT-gate design would have failed.

Figure 5D:
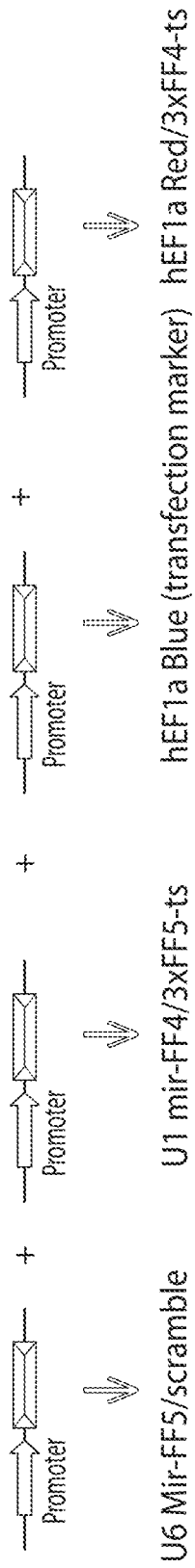
Figure 5E:
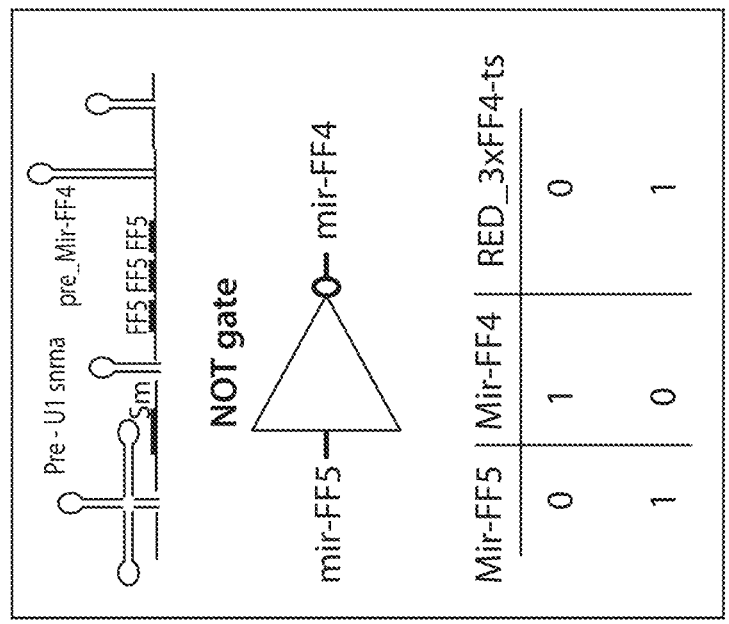
Figure 5F:
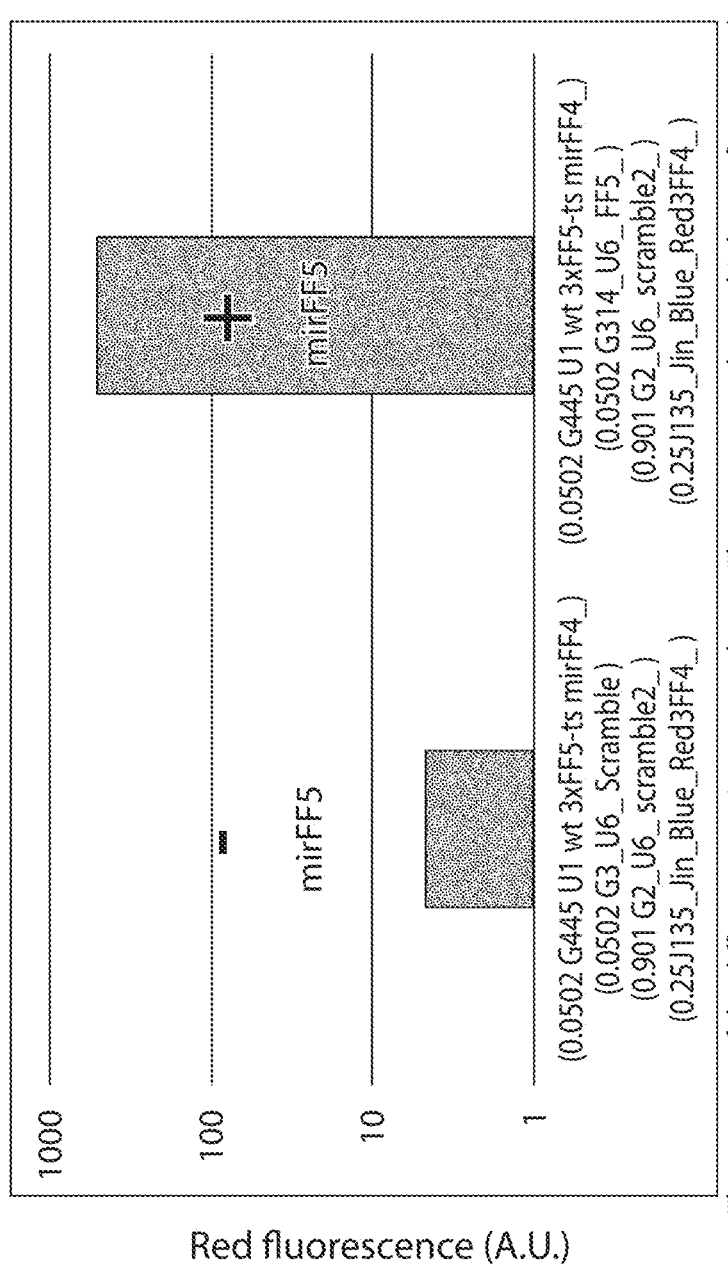

These uncertainties were resolved experimentally as shown in FIGS. 5D-5F, the flow cytometry data from HEK293FT. A red fluorescent protein with target sites for the output of the NOT-gate was used as a reporter. The data clearly showed the NOT-gate behavior.

This technology is based on the idea that, in a living cell, an RNA, instead of a protein, can transport the information on whether a micro-RNA is expressed. This transport happens from the region of the cell where the miRNA exercises its action to the region of the cell where the RNA will lead to regulation of coding or non-coding genes. The regulation can be transcriptional, like in the case of transcriptional gene silencing (FIG. 3) or post-transcriptional by starting the miRNA biogenesis. This RNA can be referred to as RNA-carrier. The region where the RNA-carrier will lead to regulation of coding or non-coding genes can be the nucleus, but this is not restricted to. The region where the miRNA targets the RNA-carrier can be the cytosol, but this is not limited to, like in the case of transcriptional gene silencing.

Once this RNA-carrier is in the proper region of the cell, which can be the nucleus but this is not limited to, it might directly start there the biogenesis of miRNAs or, like in the case of transcriptional gene silencing, it might regulate the transcription of either a pre-miRNA or other coding or non-coding RNAs.

Figure 6D:
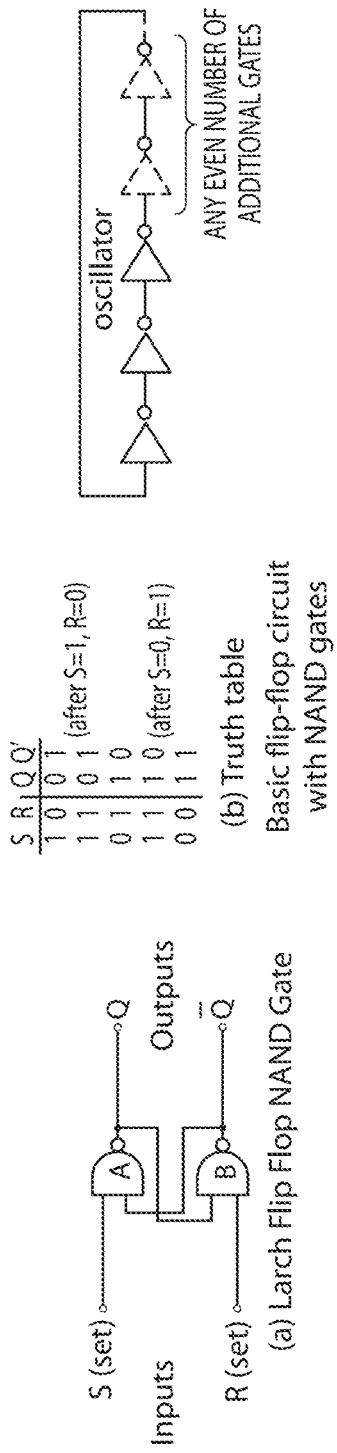
Figure 6E:
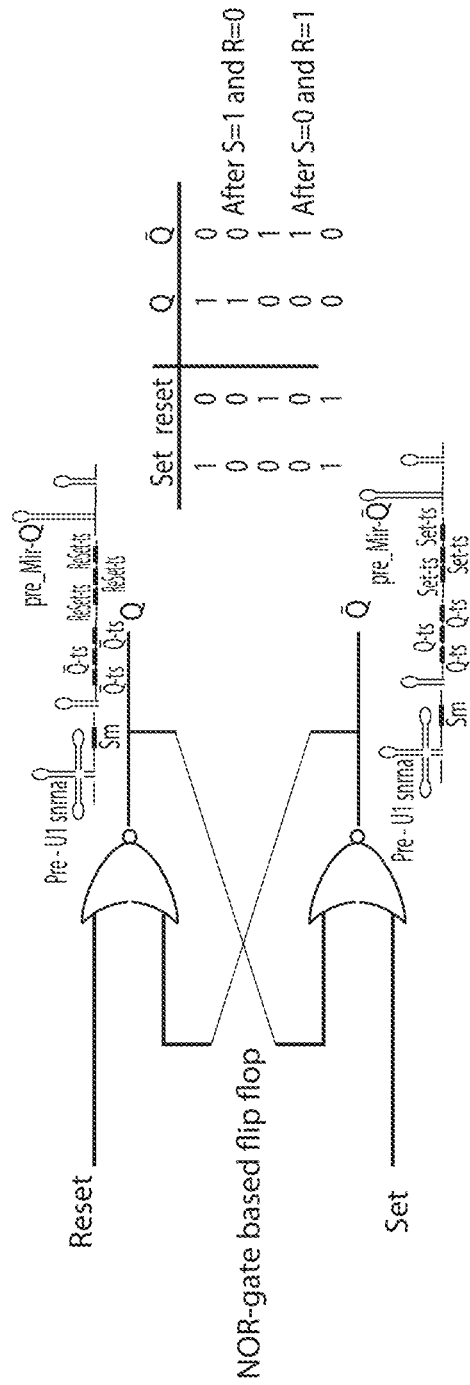

It should be noted that the miR-based NOT gate described herein is modular and can be layered to build sophisticated logic circuits. FIG. 6A shows a single module miR-based NOT gate. FIG. 6B-6C describes one example that two miR-based NOT gates can be layered to produce a miRNA-based NOR gate that can sense two individual input miRNAs and produce results accordingly. Further, FIG. 6D-6E shows other miR-based logic gate such as latch flip flop NAND gates, basic flip flop circuit NAND gates and oscillators using the miR-based NOT gate.

Figure 7A:
FIGS. 7A-7B show experimental results describing the behavior of two different NOT gates in cells.
Figure 7B:
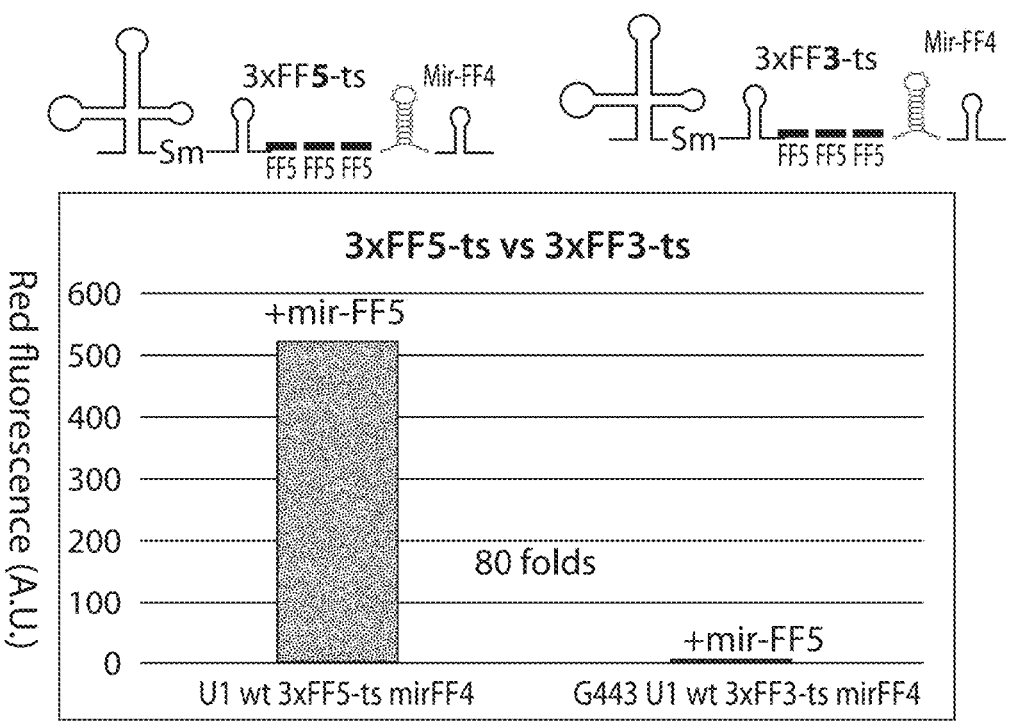

Cross-Reactivity of Different Input miRNA Signals and Target Sequences on miRNA-Based Logic Gates To test the specificity of miRNA-based NOT gates and determine whether they interact with miRNAs that are not their engineered input miRNA signal, two different mir-based NOT gates, one that senses mir-FF5, and one that senses mir-FF3, were designed. FIGS. 7A-7B show experimental results describing the behavior of two different NOT gates in cells. FIG. 7A shows the constructs that were transfected into HEK293FT cells, which encode 1) U6 Mir-FF5, 2) either U1 mir-FF4/3xFF5-ts or U1 mir-FF4/3xFF3-ts, 3) hEF1a Blue as transfection marker, and 4) hEF1a Red/3xFF4-ts as a reporter that can be downregulated in the presence of mir-FF4. FIG. 7B shows the structure of the two NOT gates, which can sense the presence of either mir-FF5 (left) or mir-FF3 (right), and the amount of Red fluorescent protein detected 4 days after transfection into HEK293FT cells as measured by flow cytometry. Mir-FF5 is present in both cases, so the U1 mir-FF4/3xFF5-ts NOT gate is bound by mir-FF5 and biogenesis of mir-FF4 does not occur, allowing Red fluorescent protein to be produced (left bar). U1 mir-FF4/3xFF3-ts interacts not with mir-FF5 but with mir-FF3, and so the presence of mir-FF5 has no effect, but the absence of mir-FF3 leads to the biogenesis of mir-FF4, suppressing expression of Red fluorescent protein. These results indicate that mir-FF5 does not interact with FF3 target sites, and so FF3 and FF5 can be used in the modular fashion described above and in FIGS. 6A-6E to design sophisticated miRNA-based logic gates such as oscillators, latch flip flop NAND gates, and basic flip flop NAND gates.

Effects of Pre-miRNA Design on Sensitivity and Specificity of miRNA-Based Logic Gates To test the effects of the pre-miRNA copy number and structure on the activity of miRNA-based logic gates, two different miRNA-based NOT gates were designed. The first gate is similar to the one depicted in FIG. 5D, and contains a single copy of pre-mir-FF4 in the form shown as Design A in FIG. 8B. The second gate is similar to the first gate, but contains two copies of pre-mir-FF4, one in Design A, and one in the form shown as Design B in FIG. 8B. FIGS. 8A-8B show experimental results describing the behavior of two different NOT gates in cells. FIG. 8A shows the constructs that were transfected into HEK293FT cells, which encode 1) either U6 Mir-FF5 or negative control, 2) either U1 mir-FF4/3xFF5 or U1 2x mir-FF4/3xFF5, 3) hEF1a Blue as transfection marker, and 4) hEF1a Red/3xFF4-ts. FIG. 8B shows the structure of the two NOT gates that sense the presence of mir-FF5 and contain one copy of pre-mir-FF4 (left) or two copies of pre-mir-FF4 that each have a different design (right), and the amount of Red fluorescent protein detected 3 days after transfection of each set of constructs into HEK293FT cells as measured by flow cytometry.

Cells transfected with the first NOT gate, with a single copy of pre-mir-FF4 of Design A (FIG. 8A), expressed little Red fluorescent protein when NOT also transfected with U6 mir-FF5, indicating biogenesis of mir-FF4 and inhibition of Red fluorescent protein production, but were 60 times more fluorescent when transfected with mir-FF5, as binding of mir-FF5 to the gate inhibited the biogenesis of mir-FF4, resulting in less inhibition and therefore greater expression of Red fluorescent protein.

Cells transfected with the second NOT gate, with two copies of pre-mir-FF4, one of Design A and one of Design B (FIG. 8B), expressed even less Red fluorescent protein when NOT also transfected with U6 mir-FF5, indicating more efficient biogenesis of mir-FF4 and inhibition of Red fluorescent protein production. These cells were 6.5 times more fluorescent when transfected with U6 mir-FF5, indicating that mir-FF5 did inhibit the biogenesis of mir-FF4 by this gate, but not as efficiently as the first gate, as some mir-FF4 was still produced by this gate, resulting in reduced Red fluorescent protein expression.

This more efficient biogenesis of output mir-FF4 by U1 2x mir-FF4/3xFF5 even in the presence of the input mir-FF5 signal occurs for two reasons—first, having two pre-miR-NAs on the RNA NOT gate increases the kinetics of Drosha binding, and pre-mir-FF4 Design B is more readily cleaved by Drosha than Design A. The combination of these elements increases the probability that Drosha will interact with this gate before it leaves the nucleus, resulting in some output miRNA biogenesis even in the presence of the input miRNA signal that is meant to prevent the generation of the output miRNA. This design is especially effective at generating the output miRNA, and may be preferred in applications intended to limit expression of the target as much as possible, and background release of the output miRNA is not deleterious, such as for targeting viral mRNAs to limit viral replication. Efficient release of antiviral miRNAs targeting viral mRNAs critical for viral replication could thus be more effective at inhibiting viral replication in infected cells, without affecting uninfected cells that do not contain the target viral mRNAs. By contrast, the first design, in which targeting of the mRNA and inhibition of expression is less efficient, is more specific, and may thus be preferred in applications where background biogenesis of the output miRNA is more deleterious. For example, if the mRNA targeted by the output miRNA encodes a critical host factor, it is important that the output miRNA be produced only under the desired conditions, or background release of the output miRNA could cause the death of healthy cells. If the output miRNA is reliably produced under only the desired conditions, then it could be designed to target a critical host factor, which may increase the therapeutic efficacy of the miRNA-based logic gate, without compromising safety.

It is to be understood that the present disclosure is not limited to these designs, and any further designs using the miR-based NOT module as basic module are encompassed herein.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An miRNA based logic gate comprising an engineered RNA carrier, wherein the engineered RNA carrier comprises:
   (i) a small nuclear RNA (snRNA) nuclear export sequence and an snRNA nuclear import sequence;
   (ii) a target site for a first microRNA (miRNA); and
   (iii) one or more pre-miRNA sequences of a second microRNA (miRNA).

2. The miRNA based logic gate of claim 1, wherein the miRNA based logic gate is a NOT gate.

3. An miRNA based logic gate, wherein the miRNA based logic gate is:
   a) a NOR gate comprising the miRNA based NOT gate of claim 2 and a target site for a third miRNA; or b) a NAND gate comprising two miRNA based NOT gates of claim 2.

4. An miRNA based logic gate, wherein the miRNA logic gate is a miRNA-based flip flop, which comprises two miRNA based NOR gates or two miRNA based NAND gates of claim 3.

5. The miRNA based logic gate of claim 1, wherein the snRNA nuclear export sequence is derived from pre-U1 snRNA, pre-U2 snRNA, pre-U3 snRNA, pre-U4 snRNA, pre-U5 snRNA, pre-U6 snRNA, pre-U7 snRNA, pre-U4atac snRNA, pre-U11 snRNA, or pre-U12 snRNA
   wherein the snRNA nuclear import sequence is derived from pre-U1 snRNA, pre-U2 snRNA, pre-U3 snRNA, pre-U4 snRNA, pre-U5 snRNA, pre-U6 snRNA, pre-U7 snRNA, pre-U4atac snRNA, pre-U11 snRNA, or pre-U12 snRNA.

6. The miRNA based logic gate of claim 1, wherein the engineered RNA carrier further comprises
   a) a sequence that binds to the survival of motor neuron complex (SMN complex); and/or
   b) a 3' cap.

7. The miRNA based logic gate of claim 1, wherein the snRNA nuclear import sequence and the snRNA nuclear export sequence are derived from the same snRNA.

8. The miRNA based logic gate of claim 1, wherein the snRNA nuclear import sequence is not a pre-U6 snRNA nuclear import sequence, wherein the snRNA nuclear export sequence is not a pre-U6 snRNA nuclear export sequence.

9. An engineered nucleic acid comprising a promoter operably linked to a nucleotide sequence encoding the miRNA based logic gate of claim 1.

10. A recombinant virus, optionally a recombinant AAV (rAAV), comprising: a viral capsid containing a promoter operably linked to a nucleotide sequence encoding the miRNA based logic gate of claim 1.

11. An isolated cell comprising the miRNA based logic gate of claim 1, optionally wherein the cell is:
    a) a prokaryotic cell, optionally a bacterial cell;
    b) a eukaryotic cell, optionally a fungal cell, plant cell, insect cell, or mammalian cell, optionally a human cell;
    c) a diseased cell; and/or
    d) from a specific tissue.

12. The isolated cell of claim 11, wherein the cell expresses the first miRNA, and does not express the second miRNA.

13. The isolated cell of claim 11, wherein the cell does not express the first microRNA, and expresses the second miRNA.

14. The isolated cell of claim 11, wherein the cell expresses both the first miRNA and the second miRNA, and downregulation of the first miRNA leads to the upregulation of the second miRNA.

15. The isolated cell of claim 11, wherein the cell expresses both the first and the second miRNA, and upregulation of the first miRNA leads to the downregulation of the second miRNA.

16. A pharmaceutical composition, comprising the miRNA based logic gate of claim 1 and a pharmaceutically acceptable carrier.

17. A method comprising delivering the miRNA based logic gate of claim 1 to a subject, optionally a human or non-human mammal, in need thereof.

18. A method for delivering a miRNA to a specific cell type in a subject, optionally a human or non-human mammal, in need thereof, comprising administering to the subject an effective amount of the miRNA based logic gate of claim 1.

19. A method for treating a disease in a subject, optionally a human or non-human mammal, in need thereof, comprising administering to the subject an effective amount of the miRNA based logic gate of claim 1.

20. The method of claim 19, wherein the subject has or is at risk of having Alpha-1 antitrypsin deficiency, Hypercholesterolemia, Hepatitis B infection, Liver adenoma due to HIV infection, Hepatitis C virus infection, Ornithine transcarbamylase deficiency, Hepatocellular carcinoma, Amyotrophic lateral sclerosis, Spinocerebellar ataxia type 1, Huntington's disease, Parkinson disease, Spinal and Bulbar muscular atrophy, Pyruvate dehydrogenase deficiency, Hyperplasia, obesity, FSHD, Nerve Injury-induced Neuropathic Pain, Age-related macular degeneration, Retinitis pigmentosa, heart failure, cardiomyopathy, cold-induced cardiovascular dysfunction, Asthma, Duchenne muscular dystrophy, or prostate cancer.

* * * * *